(12) United States Patent
Cheon et al.

(10) Patent No.: US 9,375,495 B2
(45) Date of Patent: Jun. 28, 2016

(54) MAGNETIC RESONANCE IMAGING CONTRAST AGENTS COMPRISING ZINC-CONTAINING MAGNETIC METAL OXIDE NANOPARTICLES

(75) Inventors: Jinwoo Cheon, Seoul (KR);
Young-wook Jun, Gyeonggi-do (KR);
Jung-tak Jang, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 920 days.

(21) Appl. No.: 12/527,482

(22) PCT Filed: Apr. 11, 2008

(86) PCT No.: PCT/KR2008/002050
§ 371 (c)(1),
(2), (4) Date: Jan. 4, 2010

(87) PCT Pub. No.: WO2008/127031
PCT Pub. Date: Oct. 23, 2008

(65) Prior Publication Data
US 2010/0143263 A1    Jun. 10, 2010

(30) Foreign Application Priority Data
Apr. 12, 2007 (KR) ........................ 10-2007-0036054

(51) Int. Cl.
*A61K 49/06* (2006.01)
*A61K 49/18* (2006.01)
*C01G 49/00* (2006.01)
*H01F 1/00* (2006.01)
(Continued)

(52) U.S. Cl.
CPC ......... *A61K 49/1875* (2013.01); *A61K 49/1836* (2013.01); *A61K 49/1863* (2013.01); *A61K 49/1866* (2013.01); *A61K 49/1869* (2013.01);
(Continued)

(58) Field of Classification Search
None
See application file for complete search history.

(56) References Cited

U.S. PATENT DOCUMENTS

| 4,849,210 A | 7/1989 | Widder |
| 5,023,072 A | 6/1991 | Cheng |

(Continued)

FOREIGN PATENT DOCUMENTS

| EP | 0 656 368 A1 | 6/1995 |
| KR | 10-2006-0021535 A | 3/2006 |

(Continued)

OTHER PUBLICATIONS

SW Lee, CS Kim. "Superparamagnetic properties Ni—Zn ferrite for nano-bio fusion applications." Journal of Magnetism and Magnetic Materials, vol. 304, 2006, pp. e418-e420.*

(Continued)

*Primary Examiner* — Isaac Shomer
(74) *Attorney, Agent, or Firm* — Alston & Bird LLP

(57) ABSTRACT

The present invention relates to an MRI contrast agent that includes zinc-containing water-soluble metal oxide nanoparticles and has an improved contrast effect. The zinc-containing water-soluble metal oxide nanoparticles are characterized by addition of zinc to a matrix comprising the metal oxide nanoparticles or by substitution of metal in the matrix, resulting in the improved contrast effect of MRI. In addition, the zinc-containing metal oxide nanoparticles of the present invention include the MRI contrast agent t having hybrid structures of "zinc-containing metal oxide nanoparticle—biologically/chemically active material" in which the nanoparticle is conjugated with a bioactive material such as proteins, antibodies, and chemical materials.

5 Claims, 11 Drawing Sheets

(51) Int. Cl.
*B82Y 5/00* (2011.01)
*B82Y 25/00* (2011.01)

(52) U.S. Cl.
CPC .......... *C01G 49/009* (2013.01); *C01G 49/0063* (2013.01); *H01F 1/0054* (2013.01); *B82Y 5/00* (2013.01); *B82Y 25/00* (2013.01); *C01P 2002/72* (2013.01); *C01P 2002/85* (2013.01); *C01P 2004/04* (2013.01); *C01P 2006/42* (2013.01); *Y10S 977/773* (2013.01); *Y10S 977/93* (2013.01)

(56) References Cited

U.S. PATENT DOCUMENTS

| | | | |
|---|---|---|---|
| 5,055,288 | A | 10/1991 | Lewis et al. |
| 6,203,777 | B1 | 3/2001 | Schröder |
| 6,599,498 | B1 | 7/2003 | Groman et al. |
| 6,767,635 | B1 | 7/2004 | Bahr et al. |
| 2002/0102216 | A1* | 8/2002 | Lanza et al. ............. 424/9.52 |
| 2003/0190471 | A1* | 10/2003 | Carpenter et al. ............ 428/402 |
| 2003/0219785 | A1* | 11/2003 | Hallahan et al. ................ 435/6 |
| 2005/0013778 | A1* | 1/2005 | Green et al. ................ 424/9.6 |
| 2005/0249817 | A1* | 11/2005 | Haik et al. ................... 424/617 |
| 2006/0142749 | A1* | 6/2006 | Ivkov ............................ 606/27 |
| 2006/0222594 | A1 | 10/2006 | Lee et al. |

FOREIGN PATENT DOCUMENTS

| | | |
|---|---|---|
| KR | 10-0652251 B1 | 3/2006 |
| KR | 10-2006-0043925 A | 5/2006 |
| KR | 10-0604975 B1 | 5/2006 |
| KR | 10-2006-0098213 A | 9/2006 |
| KR | 10-0713745 B1 | 4/2007 |
| WO | WO 2006/019008 A1 | 2/2006 |
| WO | WO 2006/025627 A | 3/2006 |
| WO | WO 2006/052042 A1 | 5/2006 |
| WO | WO 2007/029980 A | 3/2007 |
| WO | WO 2007/097605 A1 | 8/2007 |

OTHER PUBLICATIONS

H Deng, X Li, Q Peng, X Wang, J Chen, Y Li. "Monodisperse Magnetic Single-Crystal Ferrite Microspheres." Angew Chem. Int. Ed., vol. 44, 2005, pp. 2782-2785.*

XY Wang, GQ Yang, ZS Zhang, LM Yan, JH Meng. "Synthesis of strong-magnetic nanosized black pigment ZnxFe(3-x)O4." Dyes and Pigments, vol. 74, 2007, pp. 269-272, available online Apr. 11, 2006.*

BM Moskowitz. "Hitchhikers's Guide to Magnetism." http://www.irm.umn.edu/hg2m/hg2m_a/hg2m_a.html, accessed Feb. 6, 2012, 3 printed pages.*

SF Wnuk, CS Yuan, RT Borchardt, J Balzarini, ED Clerq, MJ Robins. "Anticancer and Antiviral Effects and Inactivation of S-Adenosyl-L-homocysteine Hydrolase with 5'-Carboxaldehydes and Oximes Synthesized from Adenosine and Sugar-Modified Analogues." Journal of Medicinal Chemistry, vol. 40, 1997, pp. 1608-1618.*

V Mohite. "Self Controlled Magnetic Hyperthermia." Florida State University College of Engineering, Masters Thesis, Fall 2004, pp. i-xii and 1-35.*

L Josephson. "BioMEMS and Biomedical Nanotechnology." "Chapter 8: Magnetic Nanoparticles for MR Imaging." ISBN 978-0-387-25842-3 (Online). 2006. pp. 1/1-6/6 and 227-237 (17 total pages).*

J Wang, C Zeng, Z Peng, Q Chen. "Synthesis and magnetic properties of Zn1-xMnxFe2O4 nanoparticles." Physics B, vol. 349, 2004, pp. 124-128.*

HM Lu, WT Zheng, Q Jiang. "Saturation magnetization of ferromagnetic and ferrimagnetic nanocrystals at room temperature." Journal of Physics D: Applied Physics. vol. 40, 2007, pp. 320-325.*

M Rozman, M Drofenik. "Hydrothermal Synthesis of Manganese Zinc Ferrites." Journal of the American Ceramic Society, vol. 78(9), 1995, pp. 2449-2455.*

C Barcena, AK Sra, GS Chaubey, C Khemtong, JP Liu, J Gao. "Zinc ferrite nanoparticles as MRI contrast agents." Chemical Communications, 2008, pp. 2224-2226.*

Ittrich et al, *Rofo* 2005, 177, 1151.

Schultz et al, *J. Magn. Mang, Mater.* 2007, 311, 464.

Valdes-Solis et al, *Nanotechnology* 2007, 18. 145603.

Jan, Jung-tak et al., "*Critical Enhancements of MRI Contrast and Hyperthermic Effects by Dopant-Controlled Magnetic Nanoparticles*"; Angew. Chem. Int. Ed. 2009, 48, pp. 1234-1238.

Extended European Search Report from corresponding European Patent Application No. 08741295.3 dated Jun. 30, 2011.

International Search Report and Written Opinion from corresponding International Application No. PCT/KR2008/002050 dated Aug. 28, 2008.

Schultz et al, *J. Magn. Mang, Mater.* 2007, 311, 464-468.

Valdis-Solis et al, *Nanotechnology* 2007, 18. 145603.

* cited by examiner (A) $Zn_xMn_{1-x}Fe_2O_4$ (B) $Zn_xFe_{3-x}O_4$ x = 0    0.1    0.2    0.3    0.4    0.8

(A) $Zn_{0.4}Mn_{0.6}Fe_2O_4$ (B) $Zn_{0.4}Fe_{2.6}O_4$

| | Element Atomic% | Zn | Mn | Fe | Zn doping level (%) | | Element Atomic% | Zn | Fe | Zn doping level (%) |
|---|---|---|---|---|---|---|---|---|---|---|
| 1 | $Zn_0MnFe_2O_4$ | 0 | 32.49 | 67.52 | 0 | 1 | $Zn_0Fe_3O_4$ | 0 | 100 | 0 |
| 2 | $Zn_{0.1}Mn_{0.9}Fe_2O_4$ | 4.12 | 29.53 | 66.35 | 10 | 2 | $Zn_{0.1}Fe_{2.9}O_4$ | 3.24 | 96.76 | 10 |
| 3 | $Zn_{0.2}Mn_{0.8}Fe_2O_4$ | 7.19 | 26.59 | 66.22 | 20 | 3 | $Zn_{0.2}Fe_{2.8}O_4$ | 6.59 | 93.41 | 20 |
| 4 | $Zn_{0.3}Mn_{0.7}Fe_2O_4$ | 10.5 | 23.95 | 65.55 | 30 | 4 | $Zn_{0.3}Fe_{2.7}O_4$ | 9.83 | 90.17 | 30 |
| 5 | $Zn_{0.4}Mn_{0.6}Fe_2O_4$ | 14.13 | 20.63 | 65.24 | 40 | 5 | $Zn_{0.4}Fe_{2.6}O_4$ | 13.22 | 86.78 | 40 |
| 6 | $Zn_{0.8}Mn_{0.2}Fe_2O_4$ | 26.51 | 6.78 | 66.71 | 80 | 6 | $Zn_{0.8}Fe_{2.2}O_4$ | 27.45 | 72.55 | 80 |

1. zinc manganese ferrite nanoparticle
2. zinc manganese ferrite - herceptin nanohybrid
3. zinc manganese ferrite - neutravidin nanohybrid ID## MAGNETIC RESONANCE IMAGING CONTRAST AGENTS COMPRISING ZINC-CONTAINING MAGNETIC METAL OXIDE NANOPARTICLES

TECHNICAL FIELD

The present invention relates to a magnetic resonance imaging contrast agent that comprises zinc-containing magnetic metal oxide nanoparticles.

BACKGROUND ART

Nanotechnology is a technique for controlling or manipulating materials at the atomic or molecular level, where various technologies are merged and is suitable for fabricating new materials and devices. The nanotechnology has wide application, such as electronics, materials, communications, machines, medicals, agricultures, energies, and environments. What makes the nano-scale particles important is that they provide unique features which micron-scale particles do not have. In particular, through controlling at nano-level, nano-scale particles may have outstanding improved materials properties, when compared to micron-scale particles.

Nano-scale magnetic materials are expected to be applied to various biomedical fields and contribute much to the growth of the fields. Magnetic nanoparticles are much smaller as compared to blood vessels and cells and are similar in size to proteins, which affords their accessibility to various types of biological tissues, and thus the magnetic nanoparticles have been used for biological diagnosis for several years. In addition, the rapid development of the nanotechnology in recent years allows manufacture of highly functional magnetic nanoparticles that can be under artificial magnetism control. At the same time, the chemical/biological stability in vivo thereof has been studied extensively.

Magnetic nanoparticles may be used in a wide variety of nano-bio technology such as molecular imaging using magnetic resonance imaging (MRI), tracking and diagnosis of diseases, hyperthermia, drugs delivery, magnetic-bio sensors, and microfluidic systems. In particular, magnetic nanoparticles can be used as a diagnostic probe for MRI. Under an external magnetic field, a magnetic moment of $\mu$ is induced in the nanoparticle. The induction field influences the spin-spin (T2) relaxation time and the spin-lattice (T1) relaxation time of the hydrogen atoms of water molecules surrounding the magnetic nanoparticles, thereby resulting in magnetic resonance signal enhancement. The imaging signal enhancement can be measured as relaxivity ($R=1/T$).

The above properties of the magnetic nanoparticles can be used for imaging the density of water proton in the tissue, the distribution of the blood vessel, diagnosis of diseases such as cancers, and the life phenomenon in a level of molecules and cells. Until now, the magnetic nanoparticle MRI contrast agent has been developed as follows:

U.S. Pat. No. 4,849,210 discloses 30 nm sized superparamagnetic magnetite particles that are incorporated into the biodegradable matrix material (proteins, carbohydrates, lipid, etc.) and their utilization in MRI of internal organs such as liver or spleen;

U.S. Pat. No. 5,023,072 discloses iron oxide superparamagnetic nanoparticles for MRI of the gastrointestinal tract. The paramagnetic, superparamagnetic and ferromagnetic particles, in combination with polysaccharide, are used for imaging of the gastrointestinal tract;

U.S. Pat. No. 5,055,288 discloses a biodegradable superparamagnetic iron oxide for vascular imaging. Individual iron oxide has a diameter of less than 50 nm and their aggregates have a diameter of less than 400 nm. Both are stable in a biological environment;

EP No. 0656368 discloses magnetic iron oxide nanoparticles that are coated with nano-sized carboxypolysaccharides. The nanoparticles are prepared by using a coprecipitation method, having a size in the range of about 2 to 7 nm, and are applied to systems such as cardiovascular system imaging and drug deliveries;

U.S. Pat. No. 6,203,777 discloses magnetite particles that are conjugated with carbohydrate. The nanoparticles are synthesized in aqueous media by using a coprecipitation method and conjugated with the carbohydrate polymers by using an ultrasonic wave reaction to be used as an MRI contrast agent for parenteral administration;

U.S. Pat. No. 6,599,498 discloses an MRI contrast agent that is coated with reduced carbohydrates and is stable against heating. The iron oxide nanoparticles are synthesized by using a coprecipitation method so as to have a size of about 10 nm, and applied to MRI for vascular systems;

US Pat. Application Publication No. US2006-0222594 discloses a magnetic nanoparticle MRI contrast agent which is capable of selective targeting, wherein iron oxide nanoparticles synthesized by a coprecipitation method are coated with micelles consisting of polymers;

Korean Patent Application Publication No. KR2006-0098213 discloses nanoparticles that are used for tumor diagnosis. The iron oxide magnetic nanoparticles that are synthesized by using high temperature thermal decomposition in an organic solvent are dissolved in water and attached to the antibody, to form a nanohybrid for tumor diagnosis.

The magnetic nanoparticles used for these MR contrast agents should fulfill the following requirements for their high performance MRI applications:

1) They should have a high magnetic moment enough to sensitively react to the external magnetic field;
2) They should exhibit excellent MR contrast effects;
3) They should be stably dispersed both in aqueous media and in vivo environments.
4) It should be feasible to conjugate them with biologically active materials; and
5) They should exhibit low toxicity and high biocompatibility.

The nanoparticle based imaging contrast agent prepared following the above-mentioned prior arts, commercially available contrast agents such as Feridex and Resovist, and iron oxide nanoparticles surrounded by water-soluble ligands have relatively low magnetic moment and poor MR contrast effect (R2). This leads to exhibit a reduced signal enhancement in MRI, and thus it has been pointed out that they have significant problems in the MRI diagnosis.

The way to resolve these problems is developing MR contrast agents comprising magnetic nanoparticles with enhanced magnetic moment. To achieve the purpose of increasing the magnetic moment, controlling the composition of metal oxide nanoparticles can be one method (Ittrich et al, *Rofo* 2005, 177, 1151; Shultz et al, *J. Magn. Magn, Mater.* 2007, 311, 464). It has been tried adding various metal dopants to iron oxide nanoparticle matrix. However, most of possible metallic dopants (e.g. Co, Ni, Mg, Ba, etc) do not increase magnetic moment and, in some cases, even reduce it after the addition (e.g. Co, Ni, Mg, Ba) (Valdés-Solís et al, *Nanotechnology* 2007, 18, 145603).

Recently, as an only one example of increasing the MRI contrast effects, Korean Patent Application Publication No. KR2006-0098213 discloses manganese-containing metal oxide nanoparticles with improved MR contrast effect. It is based on the improved magnetic moment due to the manganese. In this case, the inclusion of manganese increases magnetic moment of metal oxide by about 10%, but MR contrast effect (R2) resulted in 70~100% increase.

Therefore, it is evident that development of a new metal oxide having more improved magnetic moment is very important in maximizing the MR contrast effect.

DISCLOSURE OF INVENTION

Technical Problem

Accordingly, an object of the present invention is to provide a new metal oxide nanoparticle MRI contrast agent having a significantly improved MR signal enhancement effect and diagnosis sensitivity when compared to existing metal oxide nanoparticles. Although there have not been suggested any specific metal additives for the above object previously, the present invention discovered and showed by experiment that especially by substitution of metal in metal oxide nanoparticle matrix with zinc or by addition of zinc into the interstitial holes, it induces improved magnetic moment of metal oxide nanoparticles and the MR contrast effect. Another object of the present invention is to provide MRI contrast agent containing zinc which has high colloidal stability in aqueous media and biocompatibility.

Technical Solution

In order to accomplish the above objects, the present invention provides an MRI contrast agent that includes zinc-containing magnetic metal oxide nanoparticles, characterized in that zinc atoms/ions substitute metals in metal oxide nanoparticle matrixes or are added into vacant interstitial holes in metal oxide nanoparticle matrixes. The term "matrix" herein refers to an inorganic nanoparticle core and to a parent structure where various atoms can be added or subtracted. The metal oxide magnetic nanoparticles containing zinc are characterized by improved magnetic moment and MR signal (R2, R1) as compared to metal oxide nanoparticle matrixes without zinc.

The present invention provides an MRI contrast agent characterized in that the zinc-containing metal oxide nanoparticles are compounds in which zinc atoms/ions are added to a metal oxide matrix to substitute metals in the matrix or to be incorporated into vacant interstitial holes, wherein said metal oxide nanoparticle matrix is a compound having a chemical formula of:

(a) $M_aO_b$ ($0<a\leq16$, $0<b\leq8$, and M is a magnetic metal atom or an alloy thereof); or (b) $M_cM'_dO_e$ ($0<c\leq16$, $0<d\leq16$, $0<e\leq8$, M is a magnetic metal atom or an alloy thereof; and M' is an element selected from the group consisting of Group 1 elements, Group 2 elements, Group 12 elements, Group 13 elements, Group 14 elements, Group 15 elements, transition metal elements, lanthanide elements, and actinide elements), and wherein said zinc-containing metal oxide nanoparticles have a chemical formula of:

(c) $Zn_fM_{a-f}O_b$ ($0<f<8$, $0<a\leq16$, $0<b\leq8$, $0<f/(a-f)<10$, and M is a magnetic metal atom or an alloy thereof); or (d) $Zn_gM_{c-g}M'_dO_e$ ($0<g<8$, $0<c\leq16$, $0<d\leq16$, $0<e\leq8$, $0<g/\{(c-g)+d\}<10$, M is a magnetic metal atom or an alloy thereof; and M' is an element selected from the group consisting of Group 1 elements, Group 2 elements, Group 12 elements, Group 13 elements, Group 14 elements, Group 15 elements, transition metal elements, lanthanide elements, and actinide elements).

More preferably, the zinc-containing metal oxide nanoparticles are compounds in which zinc atoms/ions are added to a metal oxide nanoparticle matrix to substitute metals in the matrix or to be incorporated into vacant interstitial holes, wherein said metal oxide matrix is a compound having a chemical formula of:

(e) $M''_hFe_iO_j$ ($0<h\leq8$, $0<i\leq8$, $0<j\leq8$, and M'' is a magnetic metal atom or an alloy thereof); and wherein said zinc-containing metal oxide nanoparticles have a chemical formula of:

(f) $Zn_kM''_{h-k}Fe_iO_j$ ($0<k<8$, $0<h\leq16$, $0<i\leq8$, $0<j\leq8$, $0<k/\{(h-k)+i\}<10$, and M'' is a magnetic metal atom or an alloy thereof).

Most preferably, the zinc-containing metal oxide nanoparticles are compounds in which zinc is added to a metal oxide matrix to substitute matrix metals or to be incorporated into vacant interstitial holes, wherein said metal oxide matrix is a compound having a chemical formula of:

(g) $Fe_lO_m$ ($0<l\leq8$ and $0<m\leq8$); or (h) $Mn_nFe_oO_p$ ($0<n\leq8$, $0<o\leq8$, and $0<p\leq8$) and wherein said zinc-containing metal oxide nanoparticles have a chemical formula of:

(i) $Zn_qFe_{l-q}O_m$ ($0<q<8$, $0<l\leq8$, $0<m\leq8$, and $0<q/(l-q)<10$); or (j) $Zn_rMn_{n-r}Fe_oO_p$ ($0<r<8$, $0<n\leq8$, $0<o\leq8$, $0<p\leq8$, and $0<r/\{(n-r)+o\}<10$).

The zinc-containing magnetic metal oxide nanoparticles are dissolved (or dispersed) in water in itself or is dispersed in an aqueous solution due to the capping ligand or water-soluble multi-functional group ligand which surrounds each of the nanoparticles. The MRI contrast agent comprising zinc-containing magnetic metal oxide nanoparticles has excellent magnetic property (saturation magnetization) and MR contrast enhancement effect (R2 or R1) as compared to the MRI contrast agent that comprising zinc-free metal oxide magnetic nanoparticles.

In addition, the present invention provides an MRI contrast agent comprising "hybrid nanoparticles of zinc-containing metal oxide nanoparticles and biologically/chemically active materials" for diagnosis that are conjugated with bioactive materials such as antibodies and proteins and chemical materials such as fluorescent materials.

The present invention also provides an MRI contrast agent which is characterized in that it is associated with an imaging contrast agent for positron emission tomography (PET) and single photon emission computed tomography (SPECT) such as a radioisotope, an X-ray imaging contrast agent such as iodine and barium sulfate, and an ultrasonic imaging contrast agent such as microbubble.

Advantageous Effects

The zinc-containing metal oxide nanoparticles according to the present invention and the zinc-containing metal oxide hybrids nanoparticles are stable in an aqueous solution, and have the excellent magnetic property and low cytotoxicity, and the magnetic property is significantly increased as compared to the known iron oxide and manganese oxide nanoparticles, thus significantly increasing the MRI sensitivity. Zinc-containing metal oxide nanoparticles according to the present invention or zinc-containing hybrid nanoparticles conjugated with the biomaterials thereof can be used in drastic improvement on the conventional magnetic resonance image and in the diagnostic treatment system.

BRIEF DESCRIPTION OF THE DRAWINGS

FIG. 5A illustrates a TEM image of the zinc-free metal ferrite nanoparticles having the size of 15 nm. FIG. 5B illustrates a TEM image of the zinc-containing metal ferrite nanoparticles having the size of 15 nm. FIG. 5C illustrates comparison in T2 fast spin echo magnetic resonance image and R2 relaxivity coefficient of water including the nanoparticles of FIGS. 5A and 5B in the same concentration.

FIG. 10A illustrates the stability in respects to the aqueous solution according to the salt concentration. FIG. 10B illustrates the stability in respects to the aqueous solution according to the change in acidity (pH).

FIG. 11A illustrates the MR image of the mouse liver before the nanoparticle contrast agent is injected. FIGS. 11B to 11D illustrate the MR image mouse liver after the nanoparticle contrast agent is injected: immediately after the injection (11B), after 10 min (11C), and after 30 min (11D).

FIG. 14A illustrates the fluorescent photoluminescence spectrum and fluorescent image results, FIG. 14B illustrates the R2 spin-spin relaxivity coefficient of the dual mode nanoparticles, and FIG. 14C illustrates the magnetic resonance image results.

MODE FOR INVENTION

Figure 1:
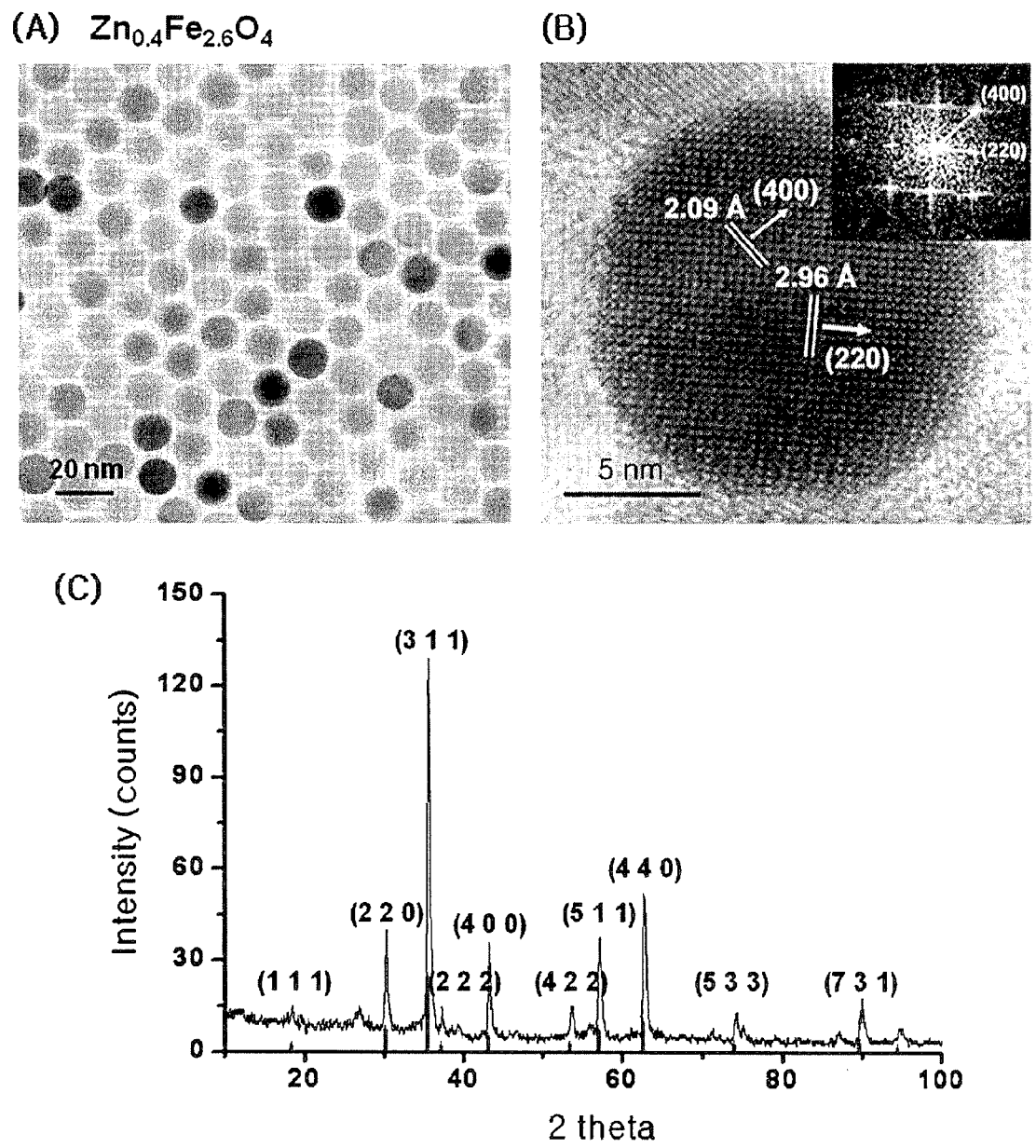
FIG. 1 illustrates (1A) an transmission electron microscopic (TEM) image (1B) a high resolution TEM and its fast Fourier transform image and (1C) an X-ray diffraction pattern analysis, of an MRI contrast agent that includes the zinc-containing ferrite magnetic nanoparticles ($Zn_{0.4}Fe_{2.6}O_4$).

The present inventors discovered that when zinc is contained in metal oxide nanoparticles with various metal additives, the magnetism is highly enhanced, and they developed an MRI contrast agent that includes zinc-containing metal oxide nanoparticles having highly enhanced magnetic properties and an improved MRI signal enhancement effect. The "zinc-containing metal oxide nanoparticles" according to the present invention are nanoparticles in which zinc atoms/ions are added to the metal oxide nanoparticle matrixes to substitute metal atoms or to be added to vacant interstitial holes. The zinc-containing metal oxide nanoparticles have the excellent magnetic moment and R2, R1 MRI signal enhancement effect, the high colloidal stability in an aqueous solution, and the low cytotoxicity due to the enhanced bio-compatibility, and are easily conjugated to a material having a biological activity and a chemical activity to satisfy the optimum condition as the MRI contrast agent.

As used in the specification of the present invention, the "zinc-containing metal oxide nanoparticles" means nanoscale particles having a diameter in the range of 1 nm to 1000 nm, preferably 2 nm to 100 nm. They are dispersed in water in the concentration in the range of 1 µg/ml~500 mg/ml, preferably 1 µg/ml~50 mg/ml. The hydrodynamic diameter of the nanoparticles is 1 nm~500 µm, preferably 1 nm~50 µm.

The "metal oxide nanoparticle matrix" means an inorganic nano-material of a mother body to which zinc is added. The metal oxide that is used as the matrix is a nanoparticle having the following chemical formula:

$M_aO_b$ (0<a≤16 and 0<b≤8, M is a magnetic metal atom or an alloy thereof); or $M_cM'_dO_e$ (0<c≤16, 0<d≤16, and 0<e≤8, M is a magnetic metal atom or an alloy thereof; and M' is an element selected from the group consisting of Group 1 elements, Group 2 elements, Group 12 elements, Group 13 elements, Group 14 elements, Group 15 elements, transition metal elements, lanthanide elements, and actinide elements, and preferably M' is an element that is selected from the group consisting of Li, Na, K, Rb, Cs, Be, Mg, Ca, Sr, Ba, Ra, Ge, Ga, In, Si, Ge, Bi, Ti, V, Cr, Mn, Fe, Co, Ni, Cu, Y, Zr, Nb, Mo, Tc, Ru, Rh, Pd, Ag, Cd, Hf, Ta, W, Re, Os, Ir, Pt, Au, Hg, lanthanide elements, and actinide elements), and it is preferably a nanoparticle having the chemical formula of $M''_hFe_iO_j$ ($0<h\leq16$, $0<i\leq8$, and $0<j\leq8$, M'' is a magnetic metal atom or an alloy thereof), and most preferably the metal oxide material is a nanoparticle having the chemical formula of $Fe_lO_m$ ($0<l\leq8$ and $0<m\leq8$), or $Mn_nFe_oO_p$ ($0<n\leq8$, $0<o\leq8$, and $0<p\leq8$).

Therefore, by substituting a portion of the metal atoms or adding to the vacant interstitial holes, they have the following formula:

$Zn_fM_{a-f}O_b$ ($0<f<8$, $0<a\leq16$, $0<b\leq8$, $0<f/(a-f)<10$, M is a magnetic metal atom or an alloy thereof); or $Zn_gM_{c-g}M'_dO_e$ ($0<g<8$, $0<c\leq16$, $0<d\leq16$, $0<e\leq8$, $0<g/\{(c-g)+d\}<10$, M is a magnetic metal atom or an alloy thereof; and M' is an element selected from the group consisting of Group 1 elements, Group 2 elements, Group 12 elements, Group 13 elements, Group 14 elements, Group 15 elements, transition metal elements, lanthanide elements, and actinide elements, and preferably M' is an element selected from the group consisting of Li, Na, K, Rb, Cs, Be, Mg, Ca, Sr, Ba, Ra, Ge, Ga, In, Si, Ge, Bi, Ti, V, Cr, Mn, Fe, Co, Ni, Cu, Y, Zr, Nb, Mo, Tc, Ru, Rh, Pd, Ag, Cd, Hf, Ta, W, Re, Os, Ir, Pt, Au, Hg, lanthanide elements, and actinide elements).

More preferably, it is a compound that includes $Zn_kM''_{h-k}Fe_iO_j$ ($0<k<8$, $0<h\leq16$, $0<i\leq8$, $0<j\leq8$, and $0<k/\{(h-k)+i\}<10$, and M'' is a magnetic metal atom or an alloy thereof), and most preferably a compound that includes $Zn_qFe_{l-q}O_m$ ($0<q<8$, $0<l\leq8$, $0<m\leq8$, and $0<q/(l-q)<10$) or $Zn_rMn_{n-r}Fe_oO_b$ ($0<r<8$, $0<n\leq8$, $0<o\leq8$, $0<p\leq8$, and $0<r/\{(n-r)+o\}<10$).

Preferably, in the zinc-containing metal oxide nanoparticles, a stoichiometric content ratio of zinc and other metal materials is as follows: $0.001<$'zinc/(entire metal material−zinc)'$<10$, preferably $0.01<$'zinc/(entire metal material−zinc)'$<1$, and more preferably $0.03<$'zinc/(entire metal material−zinc)'$<0.5$. When zinc is contained as the above, high saturation magnetization can be obtained.

In connection with this, the term 'zinc-containing' means that a zinc atom is put into a tetrahedron hole or an octahedron hole among cationic interstitial holes that are present among oxygen atoms in a crystalline structure of the metal oxide nanoparticle matrixes. Thus, when the zinc-containing water soluble or the water-dispersible metal oxide nanoparticles are grown, after the metal oxide nanoparticles that are the matrix are first synthesized, the metal atoms that are present in the tetrahedron hole or octahedron hole on the matrix are substituted with zinc, or when the metal oxide nanoparticle matrixes are growing, the metal atom and zinc are introduced simultaneously to synthesize the nanoparticles so that zinc is put into the tetrahedron hole or the octahedron hole among the cation interstitial holes of the oxygen atoms (e.g. $ZnO+Fe_2O_3\rightarrow ZnFe_2O_4$). In particular, zinc in tetrahedron hole is important because they play a role to enhance the magnetic moment of nanoparticles. The composition of metal oxide of nanoparticles where zinc is to be added may be non-stoichiometric.

The zinc-containing metal oxide nanoparticle of the present invention has superior saturation magnetization ($M_s$) or MRI contrast effect (R2 or R1) as compared to metal oxide matrix. The saturation magnetization of the zinc-containing metal oxide of the present invention is preferably 60 emu/g (magnetic atom) or more, more preferably 100 emu/g (magnetic atom) or more, and most preferably 125 emu/g (magnetic atom) or more. When a particle has the above magnetic moment, it is effective as an MRI contrast agent. In a different view, the MRI contrast effect (R2 or R1) of the zinc-containing metal oxide nanoparticle of the present invention is increased by at least 10%, more preferably at least 40%, still more preferably 100% or more, and most preferably 300% or more as compared to the metal oxide nanoparticle matrix.

As used in the present invention, the "zinc-containing metal oxide nanoparticles" means nanoparticles in which water-soluble multi-functional group ligands are bound to and they surround the zinc-containing metal oxide nanoparticles, or being capable of being dissolved or dispersed themselves in an aqueous solution without binding to a specific ligand.

The zinc-containing metal oxide nanoparticles according to the present invention can be provided in a variety of forms, the forms will depend on which zinc-containing metal oxide and the multi-functional group ligand is selected.

As used herein, the "water-soluble multi-functional group ligand" refers to a ligand that may be bound to zinc-containing nanoparticles, to solubilize in water and stabilize the nanoparticles, and to allow the nanoparticles to be bound by biologically/chemically active material.

The water soluble multi-functional group ligand can include (a) an adhesive region ($L_I$), and can further include (b) a reactive region ($L_{II}$), (c) a cross-linking region ($L_{III}$), or a reactive & cross-linking region ($L_{II}$-$L_{III}$) which includes both the reactive region ($L_{II}$) and the cross-linking region ($L_{III}$). Herein below, the water soluble multi-functional group ligand will be described in detail.

The "adhesive region ($L_I$)" means a portion of a multi-functional group ligand, comprising a functional group capable of binding to the nanoparticles, and preferably an end portion of the functional group. Accordingly, it is preferable that the adhesive region comprises a functional group having high affinity with the materials constituting the nanoparticles. Here, the nanoparticles can be attached to the adhesive regions by an ionic bond, a covalent bond, a hydrogen bond, a hydrophobic bond, or a metal-ligand coordinate covalent bond. Thus, a variety of the adhesive region of the multi-functional group ligand can be selected depending on the materials constituting the nanoparticles. For example, the adhesive region using ionic bond, covalent bond, hydrogen bond, or metal-ligand coordinate covalent bond can comprise —COOH, —NH$_2$, —SH, —CONH$_2$, —PO$_3$H, —OPO$_4$H, —SO$_3$H, —OSO$_3$H, —N$_3$, —NR$_3$OH(R=C$_n$H$_{2n+1}$, $0\leq n\leq16$), OH, —SS—, —NO$_2$, —CHO, —COX (X=F, Cl, Br, or I), —COOCO—, —CONH—, or —CN, and the adhesive region using the hydrophobic bond can comprise a hydrocarbon chain containing two or more carbon atoms, but not limited thereto.

The "reactive region ($L_{II}$)" means a portion of the multi-functional group ligand comprising a functional group capable of binding to the active materials, and preferably the other end portion of the opposite of the adhesive region. The functional group of the reactive region can be varied depending on the kinds of the active materials and their chemical formulae (see Table 1). In the present invention, the reactive region can comprise —SH, —CHO, —COOH, —NH$_2$, —OH, —PO$_3$H, —OPO$_4$H$_2$, —SO$_3$H, —OSO$_3$H, —NR$_3^+$ X$^-$ (R=C$_n$H$_m$, $0\leq n\leq16$ and $0\leq m\leq34$, X=OH, Cl, Br), NR$_4^+$ X$^-$ (R=C$_n$H$_m$, $0\leq n\leq16$, and $0\leq m\leq34$, X=OH, Cl, Br), —N$_3$, —SCOCH$_3$, —SCN, —NCS, —NCO, —CN, —F, —Cl, —I, —Br, an epoxy group, —ONO$_2$, —PO(OH)$_2$, —C=NNH$_2$, —HC=CH—, or —C≡C—, but not limited thereto.

The "cross-linking region ($L_{III}$)" means a portion of the multi-functional group ligand comprising a functional group capable of cross-linking to an adjacent multi-functional group ligand, and preferably a core portion thereof. The "cross-linking" means that the multi-functional group ligand is bound to another adjacent multi-functional group ligand by intermolecular interaction. The intermolecular interaction includes a hydrophobic interaction, a hydrogen bond, a covalent bond (for example, a disulfide bond), a Van der Waals force, and an ionic bond, but not limited thereto. Therefore, the cross-linkable functional group can be variously selected according to the kind of the intermolecular interaction. The cross-linking region can comprise, for example, —SH, —CHO, —COOH, —NH$_2$, —OH, —PO$_3$H, —OPO$_4$H$_2$, —SO$_3$H, —OSO$_3$H, —NR$_3$$^+$X$^-$ (R═C$_n$H$_m$, 0≤n≤16 and 0≤m≤34, X═OH, Cl, Br), NR$_4$$^+$X$^-$ (R═C$_n$H$_m$ 0≤n≤16, and 0≤m≤34, X═OH, Cl, Br), —N$_3$, —SCOCH$_3$, —SCN, —NCS, —NCO, —CN, —F, —Cl, —I, —Br, an epoxy group, —ONO$_2$, —PO(OH)$_2$, —C═NNH$_2$, —HC═CH—, or —C≡C—, as a functional group.

TABLE 1

Exemplary functional groups of reactive region in multi-functional group ligand

| I | II | III |
|---|---|---|
| R—NH$_2$ | R'—COOH | R—NHCO—R' |
| R—SH | R'—SH | R—SS—R' |
| R—OH | R'-(Epoxy group) | R—OCH$_2$CH(OH)—R' |
| R—NH$_2$ | R'-(Epoxy group) | R—NHCH$_2$CH(OH)—R' |
| R—SH | R'-(Epoxy group) | R—SCH$_2$CH(OH)—R' |
| R—NH$_2$ | R'—COH | R—N═CH—R' |
| R—NH$_2$ | R'—NCO | R—NHCONH—R' |
| R—NH$_2$ | R'—NCS | R—NHCSNH—R' |
| R—SH | R'—COCH$_3$ | R'—COCH$_2$S—R |
| R—SH | R'—O(C═O)X | R—S(C═O)O—R' |
| R- (Aziridine group) | R'—SH | R—CH$_2$CH(NH$_2$)CH$_2$S—R' |
| R—CH═CH$_2$ | R'—SH | R—CH$_2$CH$_2$S—R' |
| R—OH | R'—NCO | R'—NHCOO—R |
| R—SH | R'—COCH$_2$X | R—SCH$_2$CO—R' |
| R—NH$_2$ | R'—CON$_3$ | R—NHCO—R' |
| R—COOH | R'—COOH | R—(C═O)O(C═O)—R' + H$_2$O |
| R—SH | R'—X | R—S—R' |
| R—NH$_2$ | R'CH$_2$C(NH$^{2+}$)OCH$_3$ | R—NHC(NH$^{2+}$)CH$_2$—R' |
| R—OP(O$^{2-}$)OH | R'—NH$_2$ | R—OP(O$^{2-}$)—NH—R' |
| R—CONHNH$_2$ | R'—COH | R—CONHN═CH—R' |
| R—NH$_2$ | R'—SH | R—NHCO(CH$_2$)$_2$SS—R' |

(I: Functional group of reactive region in multi-functional group ligand, II: Active materials, and III: Exemplary bonds by reaction of I and II)

In the present invention, the compound which originally contains the above-described functional group can be used as a water soluble multi-functional group ligand, but a compound modified or prepared so as to have the above-described functional group by a chemical reaction known in the art can be also used as a water soluble multi-functional group ligand.

For the zinc-containing water-soluble nanoparticles according to the present invention, one example of the multi-functional group ligand is dimercaptosuccinic acid, since dimercaptosuccinic acid originally contains the adhesive region, the cross-linking region, and the reactive region. That is, —COOH on one side of the dimercaptosuccinic acid functions to be bound to the nanoparticles and COOH and SH on the other end portion functions to bind to an active materials. In the case of —SH, it can act as crosslinking region by —SS— bonding through oxidation with another —SH. In addition to the dimercaptosuccinic acid, other compounds having —COOH as the functional group of the adhesive region (L$_I$) and —COOH, —SH, or —NH$_2$ as the functional group of the reactive region (L$_{II}$) and cross-linking region (L$_{III}$) can be used as the multi-functional group ligand. Examples of the compound include dimercaptomaleic acid, and dimercaptopentadionic acid, but not limited thereto.

In the zinc-containing water soluble metal oxide nanoparticles according to the present invention, preferable other examples of the multi-functional group ligand include tetramethylamoniumhydroxide (TMAOH). TMAOH is suitable because it has an adhesive region and a reactive region. In other words, TMAOH has —OH on one side which acts for binding to a surface of a metal oxide nanoparticle and N(CH$_3$)$_4$$^+$ at its end act for binding to an active materials via ionic bond. Other than TMAOH, a compound having —OH as a functional group for an adhesive region (L$_I$) and N(CH$_3$)$_4$$^+$ or —N(CH$_3$)$_3$$^+$ as a functional group for a reactive region (L$_{II}$) can be used as a preferable multi-functional group ligand. Another example of such compound includes tetraethylamoniumhydroxide, trimethylamoniumpropanol, but not limited thereto.

In the zinc-containing water soluble metal oxide nanoparticles according to the present invention, preferable other examples of the multi-functional group ligand include peptides. Peptides are oligomers/polymers that consist of amino acids. Since the amino acids have —COOH and —NH$_2$ functional groups at both ends thereof, peptides have an attachment region and a reactive region. In addition, in particular, peptides that include one or more amino acids having one or more of —SH, —COOH, —NH$_2$ and —OH as a side chain may be used as a preferable water soluble multi-functional group ligand.

For the water soluble nanoparticles according to the present invention, another example of the preferable multi-functional group ligands is a protein. Protein is a polymer composed of more amino acids than peptides, that is, composed of several hundreds or several hundred thousands of amino acids, contains a —COOH or a —NH$_2$ functional group at its termini, and contains a lot of —COOH, —NH$_2$, —SH, —OH, —CONH$_2$, and so forth. Since protein can naturally comprise an adhesive region, a cross-linking region, and a reactive region according to its structure, as the above-described peptide, it can be useful as a multi-functional group ligand of the present invention. Representative examples of proteins which are preferable as the phase transfer ligand include a structural protein, a storage protein, a transport protein, a hormone protein, a receptor protein, a contraction protein, a defense protein, and an enzyme protein. More specifically, albumin, an antibody, a secondary antibody, an antigen, avidin, cytochrome, casein, myosin, glycinin, carotine, collagen, global protein, light protein, streptavidin, protein A, protein G, protein S, immunoglobulin, lectin, selectin, angiopoietin, anticancer protein, antibiotic protein, hormone antagonist protein, interleukin, interferon, growth factor protein, tumor necrosis factor protein, endotoxin protein, lymphotoxin protein, a tissue plasminogen activator, urokinase, streptokinase, protease inhibitor, alkyl phosphocholine, surfactant, cardiovascular pharmaceutical protein, neuro pharmaceuticals protein and gastrointestinal pharmaceuticals.

For the water-soluble nanoparticles according to the present invention, other examples of the preferable multi-functional group ligands include an amphiphilic ligand containing both of a hydrophobic region and a hydrophilic region. In the case of the nanoparticles synthesized in an organic solvent, hydrophobic ligands having long alkyl chain coat the surface. The hydrophobic region of the amphiphilic ligand, which was added at this time, and the hydrophobic ligand on the surface of the nanoparticles are bound to each other through intermolecular interaction to stabilize the nanoparticles. Further, the outermost part of the nanoparticles shows a hydrophilic functional group, and consequently water soluble nanoparticles can be prepared. Here, the intermolecular interaction includes a hydrophobic interaction, a hydrogen bond, and a Van der Waals force. Here, the portion which binds to the nanoparticles by the hydrophobic interaction is an adhesive region ($L_I$), and further the reactive region ($L_{II}$) and the cross-linking region ($L_{III}$) can be introduced therewith by an organochemical method. Further, in order to increase the stability in an aqueous solution, amphiphilic polymer ligands with multiple hydrophobic regions and multiple hydrophilic regions can be used. Cross-linking between the amphiphilic ligands can also enhance colloidal stability of the nanoparticles in aqueous media. Hydrophobic region of the amphiphilic ligand can be a linear or branched structure composed of chains containing 2 or more carbon atoms, more preferably an alkyl functional group such as ethyl, n-propyl, isopropyl, n-butyl, isobutyl, t-butyl, octyl, decyl, tetradecyl, hexadecyl, icosyl, tetracosyl, dodecyl, cyclopentyl, and cyclohexyl; a functional group having an unsaturated carbon chain containing a carbon-carbon double bond, such as ethynyl, propenyl, isopropenyl, butenyl, isobutenyl, octenyl, decenyl and oleyl; and a functional group having an unsaturated carbon chain containing a carbon-carbon triple bond, such as propynyl, isopropynyl, butynyl, isobutynyl, octynyl and decynyl. Further, examples of the hydrophilic region include a functional group being neutral at a specific pH, but being positively or negatively charged at a higher or lower pH, such as —SH, —COOH, —NH$_2$, —OH, —PO$_3$H, —OPO$_4$H$_2$, —SO$_3$H, —OSO$_3$H, and NR$_3^+$X$^-$. Preferable examples thereof include a polymer and a block copolymer, wherein monomers used therefor include acrylic acid, alkylacrylic acid, ataconic acid, maleic acid, fumaric acid, acrylamidomethylpropane sulfonic acid, vinylsulfonic acid, vinylphosphoric acid, vinyl lactic acid, styrenesulfonic acid, allylammonium, acrylonitrile, N-vinylpyrrolidone, and N-vinylformamide, but not limited thereto.

In the water soluble nanoparticles according to the present invention, preferable other examples of the multi-functional group ligand include monosaccharides, disaccharides, and a biodegradable polymer. Preferable examples of the multi-functional group ligand include glucose, mannose, fucose, N-acetyl glucomine, N-acetyl galactosamine, N-acetylneuraminic acid, fructose, xylose, sorbitol, sucrose, maltose, glycoaldehyde, dihydroxyacetone, erythrose, erythrulose, arabinose, xylulose, lactose, trehalose, mellibose, cellobiose, raffinose, melezitose, maltoriose, starchyose, estrodose, xylan, araban, hexosan, fructan, galactan, mannan, agaropectin, alginic acid, hemicellulose, hypromellose, amylose, deoxy acetone, glyceraldehyde, chitin, agarose, dextran, ribose, ribulose, galactose, carboxymethyl cellulose, glycogendextran, carbodextran, polysaccharides, cyclodextran, pullulan, cellulose, starch, glycogen, carbohydrate, polyphosphazene, polylactide, polylactide-co-glycolic acid, polycaprolactone, polyanhydride, polymaleic acid, a derivative of the polymaleic acid, polyalkylcyanoacrylate, poly hydroxybutylate, polycarbonate, polyorthoester, polyethyleneglycol, poly-L-lysine, polyglycolide, polymethyl methacrylate, polyvinylpyrrolidone and the like.

In another view, the present invention provides the zinc-containing metal oxide-biologically/chemically active material nano hybrid particles in which chemically functional molecules or biological materials having the biofunctional property are combined with the reactive region of the zinc-containing metal oxide nanoparticles.

As used in the present invention, the "hybrid nanoparticles of zinc-containing metal oxide nanoparticle and biologically/chemically active material" means nanoparticles that include the zinc-containing metal oxide nanoparticles where the multi-functional group ligand is capped and solubilized. The biologically active material (e.g.: antibodies, proteins, antigens, peptides, nucleic acids, enzymes, and cell) or chemically active material (e.g., monomers, polymers, inorganic support materials, fluorescent materials, and drugs) are conjugated to the active materials of the ligand through a covalent bond, an ionic bond, and a hydrophobic bond.

In the present invention, an example of the "hybrid nanoparticles of zinc-containing metal oxide nanoparticle and biologically/chemically active material" includes a form where the chemically functional molecules are combined with the zinc-containing metal oxide. The chemically functional molecules include a monomer, a polymer, an inorganic support, inorganic materials, biofunctional materials and the like.

In connection with this, the monomer is various types of chemicals, and examples of the monomer include an anti-cancer agent, an antibiotic, a vitamin, a drug comprising a folic acid, a fatty acid, a steroid, hormone, purine, pyrimidine, monosaccharide, and disaccharide. However, examples of the monomer are not limited thereto.

The preferable chemically functional monomer has one or more functional groups selected from —COOH, —NH$_2$, —SH, —SS—, —CONH$_2$, —PO$_3$H, —OPO$_4$H$_2$, —PO$_2$(OR$^1$)(OR$^2$)(R$^1$, R$^2$=C$_s$H$_t$N$_u$O$_w$S$_x$P$_y$X$_z$, X=—F, —Cl, —Br or —I, 0≤s≤20, 0≤t≤2(s+u)+1, 0≤u≤2s, 0≤w≤2s, 0≤x≤2s, 0≤y≤2s, 0≤z≤2s), —SO$_3$H, —OSO$_3$H, —NO$_2$, —CHO, —COSH, —COX, —COOCO—, —CORCO— (R=C$_l$H$_m$, 0≤l≤3, 0≤m≤2l+1), —COOR, —CN, —N$_3$, —N$_2$, —NROH (R=C$_s$H$_t$N$_u$O$_w$S$_x$P$_y$X$_z$, X=—F, —Cl, —Br or —I, 0≤s≤20, 0≤t≤2(s+u)+1, 0≤u≤2s, 0≤w≤2s, 0≤x≤2s, 0≤y≤2s, 0≤z≤2s), —NR$^1$NR$^2$R$^3$(R$^1$, R$^2$, R$^3$=C$_s$H$_t$N$_u$O$_w$S$_x$P$_y$X$_z$, X=—F, —Cl, —Br or —I, 0≤s≤20, 0≤t≤2(s+u)+1, 0≤u≤2s, 0≤w≤2s, 0≤x≤2s, 0≤y≤2s, 0≤z≤2s), —CONHNR$^1$R$^2$ (R$^1$, R$^2$=C$_s$H$_t$N$_u$O$_w$S$_x$P$_y$X$_z$, X=—F, —Cl, —Br or —I, 0≤s≤20, 0≤t≤2(s+u)+1, 0≤u≤2s, 0≤w≤2s, 0≤x≤2s, C$_s$H$_t$N$_u$O$_w$S$_x$P$_y$X$_z$, X=—F, —Cl, —Br, or —I, X'=F$^-$, Cl$^-$, Br$^-$, or I$^-$, 0≤s≤20, 0≤2(s+u)+1, 0≤u≤2s, 0≤w≤2s, 0≤x≤2s, 0≤y≤2s, 0≤z≤2s), —OH, —SCOCH$_3$, —F, —Cl, —Br, —I, —SCN, —NCO, —OCN, -epoxy, —C=NNH$_2$, —HC=CH—, and —C≡C—, at an end or a side chain thereof.

Examples of the polymer include dextran, carbodextran, polysaccharide, cyclodextran, pullulan, cellulose, starch, glycogen, carbohydrate, monosaccharides, disaccharides, oligosaccharides, polyphosphazene, polylactide, polylactide-co-glycolic acid, polycaprolactone, polyanhydride, polymaleic acid, a derivative of the polymaleic acid, polyalkylcyanoacrylate, poly hydroxybutylate, polycarbonate, polyorthoester, polyethyleneglycol, poly-L-lysine, polyglycolide, polymethyl methacrylate, polyvinylpyrrolidone, and the like.

Examples of the inorganic support include a metal oxide, a metal chalcogenide, an inorganic ceramic material, a carbon material, semiconductor substrate consisting of II/VI group, III/V group, and IV group elements, a metal substrate, combinations thereof, etc, and preferably it is silica (SiO$_2$), titania (TiO$_2$), indium tin oxide (ITO), nanotube, graphite, fullerene, CdS, CdSe, CdTe, ZnO, ZnS, ZnSe, ZnTe, Si, GaAs, AlAs, Au, Pt, Ag, Cu.

The inorganic material is selected from the group consisting of: a metal oxide (metal oxide that consists of at least one element selected from Group 1 and Group 2 metal elements, transition metal elements, Group 13 elements, Group 14 elements, Group 15 elements, lanthanide elements or actinide elements); a semiconductor (a semiconductor that consists of at least two elements selected from Group 13 elements, Group 12 elements, Group 14 elements, Group 15 elements and Group 16 elements); a transition metal; Group 13 elements; Group 14 elements; Group 15 elements; and Group 16 elements, but is not limited thereto.

One example of the "hybrid nanoparticles of zinc-containing metal oxide nanoparticle and biologically/chemically active material" of the present invention is configured such that the zinc-containing metal oxide nanoparticles are selectively conjugated to the biofunctional molecule. Examples of the biofunctional molecule include protein, peptide, DNA, RNA, and bio-functional drug, and preferably tissue-specific binding substances such as antigen, antibody, hapten, avidin, streptavidin, neutravidin, protein A, protein G, lectin, and selectin; pharmaceutical active materials such as an anti-cancer agent, an antibiotic, a hormone, a hormone antagonist, interleukin, interferon, a growth factor, a tumor necrosis factor, endotoxin, lymphotoxin, urokinase, streptokinase, a tissue plasminogen activator, a protease inhibitor, alkyl phosphocholine, a surfactant, cardiovascular pharmaceuticals, gastrointestinal pharmaceuticals, neuro pharmaceuticals; biologically active enzymes such as a hydrolase, a redox enzyme, a lyase, an isomerization enzyme, and a synthetase; an enzyme cofactor; and an enzyme inhibitor, but not limited thereto.

Hereinbelow, the method of preparing the water soluble zinc-containing metal oxide nanoparticles of the present invention will be described in detail.

The water soluble zinc-containing metal oxide nanoparticles according to the present invention can be obtained by using a nanoparticles synthesis method in a gas phase or a nanoparticles synthesis method in a liquid phase including an aqueous solution, an organic solvent, or a multi-solvent system, which are known in the art.

As one example of the preferable methods of preparing the nanoparticles of the present invention, the nanoparticles can be prepared through the following steps: (1) synthesizing water-insoluble nanoparticles in an organic solvent, (2) dissolving the water-insoluble nanoparticles in a first solvent, and dissolving water soluble multi-functional group ligands in a second solvent, and (3) mixing the two solutions obtained from the step (2) to conjugate the multi-functional group ligands on the surface of the water-insoluble nanoparticles followed by separation by dissolving in an aqueous solution.

Step (1) of the method relates to a process for manufacturing water-insoluble nanoparticles. In one embodiment of the present invention, water-insoluble nanoparticles can be prepared by a method comprising the steps of introducing a nanoparticle precursor to an organic solvent containing a surface stabilizer, maintaining at 50 to 600° C., preferably 100 to 600° C., for period of time for the nanoparticle precursor material to be subjected to chemical reaction for the nanoparticle growth, and then separating and purifying to prepare the resultant water-insoluble nanoparticles.

As the nanoparticle precursors, metal nitrate based compounds, metal sulfate based compounds, metal acetylacetonate based compounds, metal fluoroacetoacetate based compounds, metal halides based compounds, metal perchlororate based compounds, metal sulfamate based compounds, metal stearate based compounds, or organomatal based compounds may be used, but not limited thereto.

As the organic solvent, a benzene-based solvent, a hydrocarbon solvent, an ether-based solvent, a polymer solvent, or an ionic liquid solvent can be used, and preferably benzene, toluene, halobenzene, octane, nonane, decane, benzyl ether, phenyl ether, hydrocarbon ether, a polymer solvent, or an ionic liquid solvent can be used, but not limited thereto.

In step (2) of the preparation method, the above-prepared nanoparticles are dissolved in a first solvent, while multi-functional group ligand is dissolved in a second solvent. As the first solvent, a benzene-based solvent, a hydrocarbon solvent, an ether-based solvent, halo hydrocarbon, alcohols, a sulfoxide-based solvent, an amide-based solvent, etc. and preferably benzene, toluene, halobenzene, pentane, hexane, nonane, decane, benzyl ether, phenyl ether, and hydrocarbon ether, methylene chloride, methane bromide, methanol, and ethanol, dimethylsulfoxide, dimethylformamide can be used. As the second solvent, the solvent described above as the first solvent, as well as water can be used.

In step (3) of the preparation method, the two solutions are mixed, such that the organic surface stabilizer of the water-insoluble nanoparticles is replaced with the water soluble multi-functional group ligand. The nanoparticles replaced with the water soluble multi-functional group ligand can be separated using a method known in the art. The nanoparticles substituted with water soluble multi-functional group ligand can be separated by centrifugation or filtration. After the separation, pH is preferably adjusted to 5 to 10 through a titration step to obtain water soluble nanoparticles that are more stably dispersed.

The zinc-containing metal oxide nanoparticles prepared according to the above method have a uniform size distribution (size distribution ($\sigma$)<10%) and a high crystallinity. In addition, with the method, zinc-content in the nanoparticle matrix can be precisely controlled. In other words, by changing the ratio of zinc to other metal precursor material, the zinc content in the nanoparticle can be controlled between 0.001<'zinc/(entire metal−zinc)'<10 in a stoichiometric ratio. In particular, the disposition of zinc in the hole of a tetrahedron is facilitated, which increases magnetic moment.

In an alternative method to prepare the zinc-containing metal oxide nanoparticle MRI contrast agent, it is not necessary to prepare water-soluble nanoparticles through phase transition of nanoparticles synthesized in an organic solvent as the above method, but it can be synthesized by crystal growth through a chemical reaction in an aqueous solution of a metal precursor. This method can be carried out by a known method for synthesizing water soluble nanoparticles, which is a method for synthesizing water soluble zinc-containing metal oxide nanoparticles by adding a zinc precursor in an aqueous solution comprising a multi-functional group ligand. The zinc-containing metal oxide magnetic nanoparticles of the present invention have enhanced magneticity and MRI signal enhancing effect without being limited to a particular preparation method.

Examples of the obtained water-soluble nanoparticles are described in Table 2.

TABLE 2

Prepared zinc-containing nano particles and their properties

| No. | Matrix | Zinc content (= zinc/ total metal-zinc) | chemical formula | core size (nm) | water soluble multi-functional ligands | magnetization (emu/g) | MRI contrast effect (R2, msec$^{-1}$) |
|---|---|---|---|---|---|---|---|
| 1 | ferrite | 0.154 | $Zn_{0.4}Fe_{2.6}O_4$ | 6 | dimercapto succinic acid | 92 | |
| 2 | ferrite | 0.154 | $Zn_{0.4}Fe_{2.6}O_4$ | 6 | tetramethylammonium hydroxide | 92 | |
| 3 | ferrite | 0.154 | $Zn_{0.4}Fe_{2.6}O_4$ | 6 | BSA | 92 | |
| 4 | ferrite | 0.154 | $Zn_{0.4}Fe_{2.6}O_4$ | 6 | carbodextran | 92 | |
| 5 | ferrite | 0.154 | $Zn_{0.4}Fe_{2.6}O_4$ | 9 | dimercapto succinic acid | 108 | |

TABLE 2-continued

Prepared zinc-containing nano particles and their properties

| No. | Matrix | Zinc content (= zinc/ total metal-zinc) | chemical formula | core size (nm) | water soluble multi-functional ligands | magnetization (emu/g) | MRI contrast effect (R2, msec$^{-1}$) |
|---|---|---|---|---|---|---|---|
| 6 | ferrite | 0.154 | $Zn_{0.4}Fe_{2.6}O_4$ | 9 | tetramethylammonium hydroxide | 108 | |
| 7 | ferrite | 0.154 | $Zn_{0.4}Fe_{2.6}O_4$ | 9 | BSA | 108 | |
| 8 | ferrite | 0.154 | $Zn_{0.4}Fe_{2.6}O_4$ | 9 | carbodextran | 108 | |
| 9 | ferrite | 0.154 | $Zn_{0.4}Fe_{2.6}O_4$ | 12 | dimercapto succnic acid | 136 | |
| 10 | ferrite | 0.154 | $Zn_{0.4}Fe_{2.6}O_4$ | 12 | tetramethylammonium hydroxide | 136 | |
| 11 | ferrite | 0.154 | $Zn_{0.4}Fe_{2.6}O_4$ | 12 | BSA | 136 | |
| 12 | ferrite | 0.154 | $Zn_{0.4}Fe_{2.6}O_4$ | 12 | carbodextran | 136 | |
| 13 | ferrite | 0.034 | $Zn_{0.1}Fe_{2.9}O_4$ | 15 | dimercapto succnic acid | 126 | 0.0024 |
| 14 | ferrite | 0.034 | $Zn_{0.1}Fe_{2.9}O_4$ | 15 | tetramethylammonium hydroxide | 126 | |
| 15 | ferrite | 0.034 | $Zn_{0.1}Fe_{2.9}O_4$ | 15 | BSA | 126 | |
| 16 | ferrite | 0.034 | $Zn_{0.1}Fe_{2.9}O_4$ | 15 | carbodextran | 126 | |
| 17 | ferrite | 0.071 | $Zn_{0.2}Fe_{2.8}O_4$ | 15 | dimercapto succnic acid | 138 | 0.0031 |
| 18 | ferrite | 0.071 | $Zn_{0.2}Fe_{2.8}O_4$ | 15 | tetramethylammonium hydroxide | 138 | |
| 19 | ferrite | 0.071 | $Zn_{0.2}Fe_{2.8}O_4$ | 15 | BSA | 138 | |
| 20 | ferrite | 0.071 | $Zn_{0.2}Fe_{2.8}O_4$ | 15 | carbodextran | 138 | |
| 21 | ferrite | 0.111 | $Zn_{0.3}Fe_{2.7}O_4$ | 15 | dimercapto succnic acid | 152 | 0.0038 |
| 22 | ferrite | 0.111 | $Zn_{0.3}Fe_{2.7}O_4$ | 15 | tetramethylammonium hydroxide | 152 | |
| 23 | ferrite | 0.111 | $Zn_{0.3}Fe_{2.7}O_4$ | 15 | BSA | 152 | |
| 24 | ferrite | 0.111 | $Zn_{0.3}Fe_{2.7}O_4$ | 15 | carbodextran | 152 | |
| 25 | ferrite | 0.154 | $Zn_{0.4}Fe_{2.6}O_4$ | 15 | dimercapto succnic acid | 161 | 0.0045 |
| 26 | ferrite | 0.154 | $Zn_{0.4}Fe_{2.6}O_4$ | 15 | tetramethylammonium hydroxide | 161 | |
| 27 | ferrite | 0.154 | $Zn_{0.4}Fe_{2.6}O_4$ | 15 | BSA | 161 | |
| 28 | ferrite | 0.154 | $Zn_{0.4}Fe_{2.6}O_4$ | 15 | carbodextran | 161 | |
| 29 | ferrite | 0.154 | $Zn_{0.4}Fe_{2.6}O_4$ | 15 | hypromelose | 161 | |
| 30 | ferrite | 0.154 | $Zn_{0.4}Fe_{2.6}O_4$ | 15 | neutravidin | 161 | |
| 31 | ferrite | 0.154 | $Zn_{0.4}Fe_{2.6}O_4$ | 15 | antibody (IgG) | 161 | |
| 32 | ferrite | 0.364 | $Zn_{0.8}Fe_{2.2}O_4$ | 15 | dimercapto succnic acid | 115 | 0.0016 |
| 33 | ferrite | 0.364 | $Zn_{0.8}Fe_{2.2}O_4$ | 15 | tetramethylammonium hydroxide | 115 | |
| 34 | manganese ferrite | 0.154 | $Zn_{0.4}Mn_{0.6}Fe_2O_4$ | 6 | dimercapto succnic acid | 107 | |
| 35 | manganese ferrite | 0.154 | $Zn_{0.4}Mn_{0.6}Fe_2O_4$ | 6 | tetramethylammonium hydroxide | 107 | |
| 36 | manganese ferrite | 0.154 | $Zn_{0.4}Mn_{0.6}Fe_2O_4$ | 6 | BSA | 107 | |
| 37 | manganese ferrite | 0.154 | $Zn_{0.4}Mn_{0.6}Fe_2O_4$ | 6 | carbodextran | 107 | |
| 38 | manganese ferrite | 0.154 | $Zn_{0.4}Mn_{0.6}Fe_2O_4$ | 9 | dimercapto succnic acid | 129 | |
| 39 | manganese ferrite | 0.154 | $Zn_{0.4}Mn_{0.6}Fe_2O_4$ | 9 | tetramethylammonium hydroxide | 129 | |
| 40 | manganese ferrite | 0.154 | $Zn_{0.4}Mn_{0.6}Fe_2O_4$ | 9 | BSA | 129 | |
| 41 | manganese ferrite | 0.154 | $Zn_{0.4}Mn_{0.6}Fe_2O_4$ | 9 | carbodextran | 129 | |
| 42 | manganese ferrite | 0.071 | $Zn_{0.2}Mn_{0.8}Fe_2O_4$ | 12 | dimercapto succnic acid | 135 | |
| 43 | manganese ferrite | 0.071 | $Zn_{0.2}Mn_{0.8}Fe_2O_4$ | 12 | tetramethylammonium hydroxide | 135 | |
| 44 | manganese ferrite | 0.071 | $Zn_{0.2}Mn_{0.8}Fe_2O_4$ | 12 | BSA | 135 | |
| 45 | manganese ferrite | 0.071 | $Zn_{0.2}Mn_{0.8}Fe_2O_4$ | 12 | carbodextran | 135 | |
| 46 | manganese ferrite | 0.111 | $Zn_{0.3}Mn_{0.7}Fe_2O_4$ | 12 | dimercapto succnic acid | 146 | |
| 47 | manganese ferrite | 0.111 | $Zn_{0.3}Mn_{0.7}Fe_2O_4$ | 12 | tetramethylammonium hydroxide | 146 | |
| 48 | manganese ferrite | 0.111 | $Zn_{0.3}Mn_{0.7}Fe_2O_4$ | 12 | BSA | 146 | |
| 49 | manganese ferrite | 0.111 | $Zn_{0.3}Mn_{0.7}Fe_2O_4$ | 12 | carbodextran | 146 | |
| 50 | manganese ferrite | 0.154 | $Zn_{0.4}Mn_{0.6}Fe_2O_4$ | 12 | dimercapto succnic acid | 153 | |
| 51 | manganese ferrite | 0.154 | $Zn_{0.4}Mn_{0.6}Fe_2O_4$ | 12 | tetramethylammonium hydroxide | 153 | |
| 52 | manganese ferrite | 0.154 | $Zn_{0.4}Mn_{0.6}Fe_2O_4$ | 12 | BSA | 153 | |
| 53 | manganese ferrite | 0.154 | $Zn_{0.4}Mn_{0.6}Fe_2O_4$ | 12 | carbodextran | 153 | |
| 54 | manganese ferrite | 0.154 | $Zn_{0.4}Mn_{0.6}Fe_2O_4$ | 12 | hypromelose | 153 | |
| 55 | manganese ferrite | 0.154 | $Zn_{0.4}Mn_{0.6}Fe_2O_4$ | 12 | neutravidin | 153 | |
| 56 | manganese ferrite | 0.154 | $Zn_{0.4}Mn_{0.6}Fe_2O_4$ | 12 | antibody(IgG) | 153 | |
| 57 | manganese ferrite | 0.034 | $Zn_{0.1}Mn_{0.9}Fe_2O_4$ | 15 | dimercapto succnic acid | 140 | 0.0034 |
| 58 | manganese ferrite | 0.034 | $Zn_{0.1}Mn_{0.9}Fe_2O_4$ | 15 | tetramethylammonium hydroxide | 140 | |
| 59 | manganese ferrite | 0.034 | $Zn_{0.1}Mn_{0.9}Fe_2O_4$ | 15 | BSA | 140 | |
| 60 | manganese ferrite | 0.034 | $Zn_{0.1}Mn_{0.9}Fe_2O_4$ | 15 | carbodextran | 140 | |
| 61 | manganese ferrite | 0.071 | $Zn_{0.2}Mn_{0.8}Fe_2O_4$ | 15 | dimercapto succnic acid | 154 | 0.0041 |
| 62 | manganese ferrite | 0.071 | $Zn_{0.2}Mn_{0.8}Fe_2O_4$ | 15 | tetramethylammonium hydroxide | 154 | |
| 63 | manganese ferrite | 0.071 | $Zn_{0.2}Mn_{0.8}Fe_2O_4$ | 15 | BSA | 154 | |

TABLE 2-continued

Prepared zinc-containing nano particles and their properties

| No. | Matrix | Zinc content (= zinc/total metal- zinc) | chemical formula | core size (nm) | water soluble multi-functional ligands | magnetization (emu/g) | MRI contrast effect (R2, msec$^{-1}$) |
|---|---|---|---|---|---|---|---|
| 64 | manganese ferrite | 0.071 | $Zn_{0.2}Mn_{0.8}Fe_2O_4$ | 15 | carbodextran | 154 | |
| 65 | manganese ferrite | 0.111 | $Zn_{0.3}Mn_{0.7}Fe_2O_4$ | 15 | dimercapto succnic acid | 166 | 0.0046 |
| 66 | manganese ferrite | 0.111 | $Zn_{0.3}Mn_{0.7}Fe_2O_4$ | 15 | tetramethylammonium hydroxide | 166 | |
| 67 | manganese ferrite | 0.111 | $Zn_{0.3}Mn_{0.7}Fe_2O_4$ | 15 | BSA | 166 | |
| 68 | manganese ferrite | 0.111 | $Zn_{0.3}Mn_{0.7}Fe_2O_4$ | 15 | carbodextran | 166 | |
| 69 | manganese ferrite | 0.154 | $Zn_{0.4}Mn_{0.6}Fe_2O_4$ | 15 | dimercapto succnic acid | 175 | 0.0052 |
| 70 | manganese ferrite | 0.154 | $Zn_{0.4}Mn_{0.6}Fe_2O_4$ | 15 | tetramethylammonium hydroxide | 175 | |
| 71 | manganese ferrite | 0.154 | $Zn_{0.4}Mn_{0.6}Fe_2O_4$ | 15 | BSA | 175 | |
| 72 | manganese ferrite | 0.154 | $Zn_{0.4}Mn_{0.6}Fe_2O_4$ | 15 | carbodextran | 175 | |
| 73 | manganese ferrite | 0.154 | $Zn_{0.4}Mn_{0.6}Fe_2O_4$ | 15 | hypromelose | 175 | |
| 74 | manganese ferrite | 0.154 | $Zn_{0.4}M_{0.6}Fe_2O_4$ | 15 | neutravidin | 175 | |
| 75 | manganese ferrite | 0.154 | $Zn_{0.4}Mn_{0.6}Fe_2O_4$ | 15 | antibody (IgG) | 175 | |
| 76 | manganese ferrite | 0.364 | $Zn_{0.8}Mn_{0.2}Fe_2O_4$ | 15 | dimercapto succnic acid | 138 | 0.0036 |
| 77 | manganese ferrite | 0.364 | $Zn_{0.8}Mn_{0.2}Fe_2O_4$ | 15 | tetramethylammonium hydroxide | 138 | |
| 78 | cobalt ferrite | 0.111 | $Zn_{0.3}Co_{0.7}Fe_2O_4$ | 12 | dimercapto succnic acid | | |
| 79 | cobalt ferrite | 0.111 | $Zn_{0.3}Co_{0.7}Fe_2O_4$ | 12 | tetramethylammonium hydroxide | | |
| 80 | cobalt ferrite | 0.111 | $Zn_{0.3}Co_{0.7}Fe_2O_4$ | 12 | BSA | | |
| 81 | cobalt ferrite | 0.111 | $Zn_{0.3}Co_{0.7}Fe_2O_4$ | 12 | carbodextran | | |
| 82 | cobalt ferrite | 0.154 | $Zn_{0.4}Co_{0.6}Fe_2O_4$ | 12 | dimercapto succnic acid | | |
| 83 | cobalt ferrite | 0.154 | $Zn_{0.4}Co_{0.6}Fe_2O_4$ | 12 | tetramethylammonium hydroxide | | |
| 84 | cobalt ferrite | 0.154 | $Zn_{0.4}Co_{0.6}Fe_2O_4$ | 12 | BSA | | |
| 85 | cobalt ferrite | 0.154 | $Zn_{0.4}Co_{0.6}Fe_2O_4$ | 12 | carbodextran | | |
| 86 | nickel ferrite | 0.111 | $Zn_{0.3}Ni_{0.7}Fe_2O_4$ | 12 | dimercapto succnic acid | | |
| 87 | nickel ferrite | 0.111 | $Zn_{0.3}Ni_{0.7}Fe_2O_4$ | 12 | tetramethylammonium hydroxide | | |
| 88 | nickel ferrite | 0.111 | $Zn_{0.3}Ni_{0.7}Fe_2O_4$ | 12 | BSA | | |
| 89 | nickel ferrite | 0.111 | $Zn_{0.3}Ni_{0.7}Fe_2O_4$ | 12 | carbodextran | | |
| 90 | nickel ferrite | 0.154 | $Zn_{0.4}Ni_{0.6}Fe_2O_4$ | 12 | dimercapto succnic acid | | |
| 91 | nickel ferrite | 0.154 | $Zn_{0.4}Ni_{0.6}Fe_2O_4$ | 12 | tetramethylammonium hydroxide | | |
| 92 | nickel ferrite | 0.154 | $Zn_{0.4}Ni_{0.6}Fe_2O_4$ | 12 | BSA | | |
| 93 | nickel ferrite | 0.154 | $Zn_{0.4}Ni_{0.6}Fe_2O_4$ | 12 | carbodextran | | |
| 94 | manganese oxide | 0.154 | $Zn_{0.4}Mn_{2.6}O_4$ | 6 | tetramethylammonium hydroxide | | |
| 95 | manganese oxide | 0.154 | $Zn_{0.4}Mn_{2.6}O_4$ | 6 | BSA | | |
| 96 | manganese oxide | 0.154 | $Zn_{0.4}Mn_{2.6}O_4$ | 6 | carbodextran | | |
| 97 | cobalt oxide | 0.25 | $Zn_{0.2}Co_{0.8}O$ | 7 | tetramethylammonium hydroxide | | |
| 98 | cobalt oxide | 0.25 | $Zn_{0.2}Co_{0.8}O$ | 7 | BSA | | |
| 99 | cobalt oxide | 0.25 | $Zn_{0.2}Co_{0.8}O$ | 7 | carbodextran | | |
| 100 | nickel oxide | 0.25 | $Zn_{0.2}Ni_{0.8}O$ | 10 | tetramethylammonium hydroxide | | |
| 101 | nickel oxide | 0.25 | $Zn_{0.2}Ni_{0.8}O$ | 10 | BSA | | |
| 102 | nickel oxide | 0.25 | $Zn_{0.2}Ni_{0.8}O$ | 10 | carbodextran | | |

Hereinafter, the application of the MRI contrast agent that includes the zinc-containing water soluble metal oxide nano material will be described in detail.

The "zinc-containing metal oxide nanoparticles" of the present invention has a superior magnetic moment when compared with the conventional MRI contrast agents comprising metal oxide nanoparticles, and thus it can allow a higher level of high-sensitivity diagnosis. Further, as compared with the conventionally used MRI contrast agent, even a small amount can provide an effect of enhancing the signals to a desired level. Accordingly, they can be used as a contrast agent having lower biological toxicity and side-effects than conventional materials.

Since the zinc-containing water-soluble metal oxide nanoparticles have the excellent R2, R1 MRI signal amplification effect as compared to conventional iron oxide nanoparticles, a diagnosis of diseases at an early stage and the detection of biomolecules in a very small amount are possible. In general, on the surface of a site where cancer cells, cerebrovascular accidents, or myocardial infarctions occur, there is an over-expressed biomarker. The material that has the target specificity and can be selectively bound with the biomarker (e.g. biopolymers and chemical molecules such as antibodies, proteins, nucleic acids, enzymes or the like) may be obtained by using a method that has been known in the art. Alternatively, a known material may be used. The material having the target specificity that is obtained by using the above method may be conjugated with the reactive region of the zinc-containing water soluble metal oxide nanoparticles to synthesize the hybrid nanoparticles, which can detect the a site or tissue causing diseases. Accordingly, the magnetic particles label the diseased portion and show the MRI signal, thus achieving a diagnosis.

Proteins associated with zinc, which is contained in the MRI contrast agent of the present invention and is an essential element in a human body, act mainly as an enzyme to play an important role in an activation of metabolism. Therefore, like the ferrite-based imaging contrast agent, zinc-containing metal oxide nanoparticles are bio-compatible and reduced toxicity.

The water-soluble zinc-containing metal oxide nanoparticles can be also coupled to other diagnostic probes and used as a double- or multiple-diagnostic probe.

With respect to the MRI contrast agent according to the present invention, such as a radioactive isotope, an X-ray imaging contrast agent such as iodine and barium sulfate, and an ultrasonic imaging contrast agent such as microbubble may be bonded to the zinc-containing water soluble metal oxide nanoparticles. The resulting MRI contrast agent may be applied to a single photon emission computer tomography (SPECT) or a positron emission tomography (PET) and computed tomography (CT).

In addition, with respect to the MRI contrast agent according to the present invention, a fluorescent material may be bonded to the zinc-containing water soluble metal oxide nanoparticles. This MRI contrast agent may be applied to the optical imaging and the spectroscopy.

EXAMPLES

Example 1

Synthesis of a Zinc-Containing Ferrite Nanoparticle MRI Contrast Agent of $Zn_xM_{1-x}Fe_2O_4$ (M=Fe or Mn, x=0.1, 0.2, 0.3, 0.4, and 0.8) Having the Core Size of 15 nm and Coated with Dimercaptosuccinic Acid The zinc-containing ferrite nanoparticle MRI contrast agent of $Zn_xM_{1-x}Fe_2O_4$ (M=Fe or Mn, x=0.1, 0.2, 0.3, 0.4, and 0.8) having the core size of 15 nm was synthesized as an example of the MRI contrast agent comprising the zinc-containing metal oxide nanoparticles described in the specification of the present invention, by the methods disclosed in Korean Patent Nos. 10-0604975, 10-0652251, and 10-0713745, PCT/KR2004/002509, Korean Patent No. 10-0604975, PCT/KR2004/003088, PCT/KR2007/001001 and Korean Patent Application No. 2006-0018921. $ZnCl_2$, $FeCl_2$ or $MnCl_2$, and $Fe(acac)_3$ (acac=acetylacetonate) were added to a trioctylamine solvent in which 20 mmol oleic acid and oleylamine were contained. The reaction was performed at 200° C. and at 300° C. for 2 hour, to synthesize 15 nm $Zn_xM_{1-x}Fe_2O_4$ (M=Fe or Mn, x=0.1, 0.2, 0.3, 0.4, and 0.8) nanoparticles. In order to control the content ratio of zinc so that x was in the range of 0.1 to 0.8, the ratio of $ZnCl_2$ and $FeCl_2$ that were the precursor materials were increased or reduced by using the same method. The prepared zinc-containing ferrite nanoparticles were precipitated with an excessive amount of ethanol, and the separated nanoparticles were redispersed in toluene to obtain a colloidal solution.

Thereafter, the DMSO solution in which the dimercaptosuccinic acid was dissolved in an excessive amount was added to the nanoparticles that were dispersed in toluene in an amount of 20 mg/ml and then reacted for 2 hours, and the nanoparticles were subjected to centrifugation and then dispersed in water.

Figure 2:
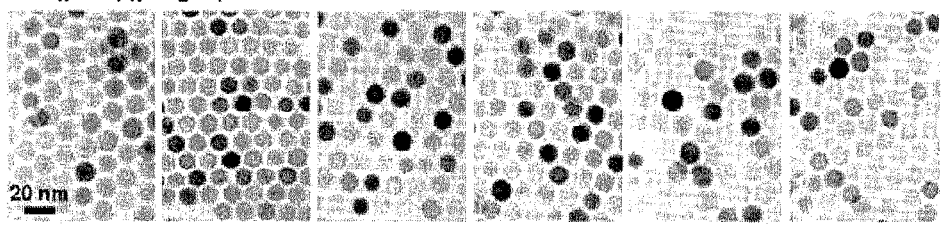
FIG. 2 illustrates TEM images of MRI contrast agents that includes the zinc-containing ferrite magnetic nanoparticles with various zinc contents (2A) $Zn_xMn_{1-x}Fe_2O_4$ (x=0, 0.1, 0.2, 0.3, 0.4, 0.8), (2B) $Zn_xFe_{3-x}O_4$ (x=0, 0.1, 0.2, 0.3, 0.4, 0.8).
Figure 2:
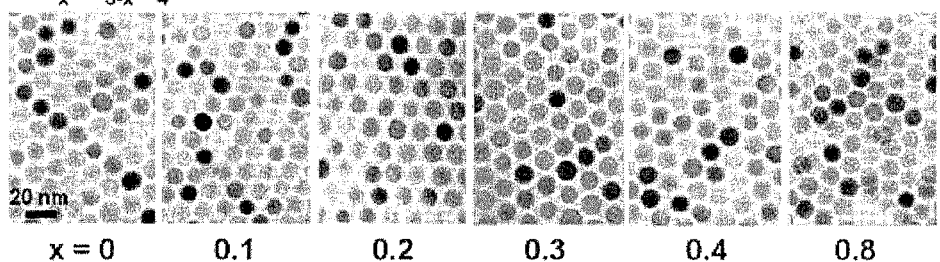
Figure 3:
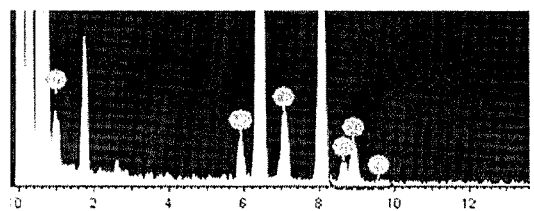
FIG. 3 illustrates energy dispersive analyses of X-ray (EDAX) MRI contrast agents that includes the zinc-containing ferrite magnetic nanoparticles of (3A) $Zn_xMn_{1-x}Fe_2O_4$ (x=0, 0.1, 0.2, 0.3, 0.4, 0.8), (3B) $Zn_xFe_{3-x}O_4$ (x=0, 0.1, 0.2, 0.3, 0.4, 0.8).
Figure 3:
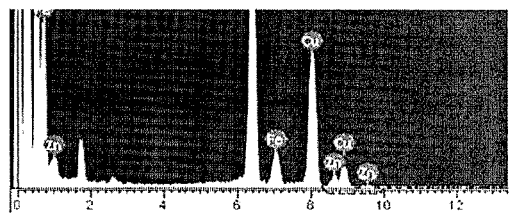

FIG. 1A and FIG. 2 illustrates $Z_xM_{1-x}Fe_2O_4$ (M=Fe or Mn, x=0, 0.1, 0.2, 0.3, 0.4, and 0.8) which has been obtained by the above method and has a uniform sphere shape with 15 nm in size (size distribution σ<10%). Through the high resolution TEM (FIG. 1B) and the X-ray diffraction pattern (XRD) (FIG. 1C), the nanoparticles have a spinel structure and high crystallinity. The content of zinc was analyzed by the inductively coupled plasma-mass spectroscopy (ICP-MS) and the energy dispersive atomic emission spectra of X-ray (EDAX) and it was confirmed that the zinc content can be precisely controlled (FIG. 3).

The zinc content, the core size, the used water soluble multi-functional group ligand, the magnetic moment, and the MRI contrast effect of the nanoparticles according to the present invention are shown in Table 2, Numbers 13~33, and 57~77.

Example 2

Synthesis of a Zinc-Containing Ferrite Nanoparticle MRI Contrast Agents of $Zn_{0.4}M_{0.6}Fe_2O_4$ (M=Fe or Mn) Having the Core Sizes of 6, 9, and 12 nm and Coated with Dimercaptosuccinic Acid 10 mmol oleic acid and 30 mmol oleylamine were added in conjunction with $ZnCl_2$, $FeCl_2$ or $MnCl_2$, and $Fe(acac)_3$ to a trioctylamine solvent. The solution was subjected to a thermal decomposition at 180° C. and 250° C. for 3 hours, to synthesize 6 nm $Zn_{0.4}M_{0.6}Fe_2O_4$ (M=Fe or Mn) nanoparticles. In order to synthesize the nanoparticles having different sizes of 9 nm and 12 nm, the precursor materials were added in the same amount to the trioctylamine solution in which the ratio of the oleic acid and oleylamine was changed, and heated and reacted with each other by using the same method and then performing the precipitation.

Thereafter, the DMSO solution in which the dimercaptosuccinic acid was dissolved in an excessive amount was added to the nanoparticles that were dispersed in toluene in an amount of 20 mg/ml and then reacted for 2 hours, and the nanoparticles were subjected to centrifugal separation and then dispersed in water.

The nanoparticles that were synthesized by using the above-mentioned method had the spherical shape and the very uniform size, and the content of zinc was analyzed by using the ICP-MS and the EDAX. The zinc content, the core size, the used water soluble multi-functional group ligand, and the magnetization of the nanoparticles according to the present invention are shown in Table 2, Numbers 1~12 and 34~56.

Example 3

Synthesis of a Zinc-Containing Cobalt Ferrite Nanoparticle MRI Contrast Agent of $Zn_xM_{1-x}Fe_2O_4$ (M=Co or Ni, x=0.3 and 0.4) Having the Core Size of 12 nm and Coated with the Dimercaptosuccinic Acid The zinc-containing ferrite nanoparticle MRI contrast agent of $Zn_xM_{1-x}Fe_2O_4$ (M=Co or Ni, x=0.3 and 0.4) having the core size of 12 nm was synthesized by using the following methods, as an example of the MRI contrast agent comprising the zinc-containing metal oxide nanoparticles of the present invention. The nanoparticles were synthesized 20 mmol oleic acid and oleylamine were added in conjunction with $ZnCl_2$, $CoCl_2$ or $NiCl_2$, and $Fe(acac)_3$ to a trioctylamine solvent. The solution is subjected to a thermal decomposition under 200° C. and 300° C. for 2 hours, to synthesize $Zn_{0.3}M_{0.7}Fe_2O_4$ (M=Co or Ni) nanoparticles of 12 nm in size. In order to synthesize the nanoparticles having different sizes of 9 nm and 12 nm, the precursor materials were added in the same amount to the trioctylamine solution in which the ratio of the oleic acid and oleylamine was controlled.

Thereafter, the DMSO solution in which dimercaptosuccinic acid was dissolved in an excessive amount was added to the nanoparticles that were dispersed in toluene in an amount of 20 mg/ml and then reacted for 2 hours, and the nanoparticles were subjected to centrifugal separation and then dispersed in water.

The nanoparticles that were synthesized by using the above-mentioned method had the spherical shape and the very uniform size, and the content of zinc was analyzed by using the ICP-MS and EDAX. The zinc content, the core size, and the used water soluble multi-functional group ligand of the nanoparticles according to the present invention are shown in Table 2, Numbers 78~93.

Example 4

Synthesis of a Zinc-Containing Oxide Nanoparticle MRI Contrast Agent of $Zn_xM_yO_z$ (M=Mn, Co, or Ni) Coated with Tetramethylamonium Hydroxide (TMAOH)

The zinc-containing manganese oxide nanoparticle MRI contrast agent of $Zn_xM_yO_z$ (M=Mn, Co, or Ni) composition was synthesized, as an example of the MRI contrast agent comprising the zinc-containing metal oxide nanoparticles described in the specification of the present invention, by using the following methods. $ZnCl_2$ and $MCl_2$ (M=Mn, Co, or Ni) were dispersed in a trioxtyl amine solution in which oleic acid and oleylamine were contained in an amount of 0.5 mmol and 6.5 mmol, heated to 270° C. for 1 hr, to synthesize 12 nm $Zn_xM_yO_z$ (M=Mn, Co, or Ni) nanoparticles. The zinc-containing oxide nanoparticles that were synthesized by using the above method and dispersed in 1 ml of toluene in a concentration of 50 mg/ml were precipitated with an excessive amount of ethanol, and redispersed in 5 ml TMAOH solution. The synthesized nanoparticles had the $Zn_{0.4}Mn_{2.6}O_4$, $Zn_{0.2}CO_{0.8}O$, or $Zn_{0.2}Ni_{0.8}O$ compositions and the core sizes of 6, 7, and 10 nm. The content of zinc was analyzed by using the ICP-MS and EDAX. The zinc content, the core size, and the used water soluble multi-functional group ligand of the nanoparticles according to the present invention are shown in Table 2, Numbers 94~102.

Example 5

Figure 4:
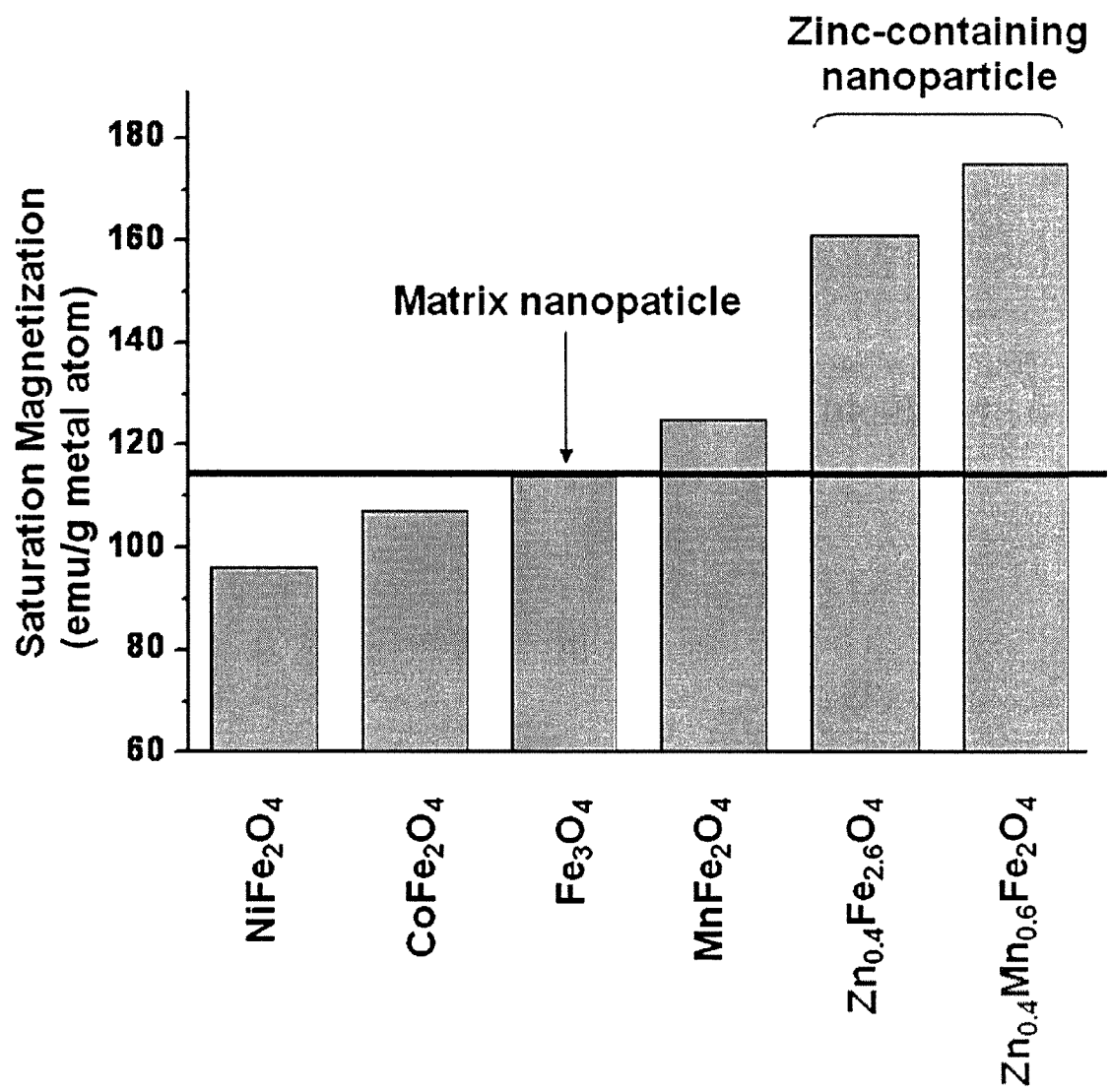
FIG. 4 illustrates the comparison in saturation magnetization of the nanoparticles where various types of metal additives are incorporated into $Fe_3O_4$ nanoparticles used as matrix.

Comparison of Saturation Magnetization of Iron Oxide Nanoparticle Matrix Containing Various Types of Metal Additive In order to see what kind of metal additive increases saturation magnetization of nanoparticle matrix, iron oxide nanoparticle containing various types of metal additive (Ni, Co, Mn, or Zn) was synthesized in the same size (15 nm) and saturation magnetization ($M_s$) was measured with MPMS Superconducting Quantum Interference Device (SQUID) Magnetometer. Iron oxide nanoparticles containing iron oxide and Ni, Co and Mn were prepared by the methods disclosed in Korean Patent Nos. 10-0604975, 10-0652251, and 10-0713745, PCT/KR2004/002509, Korean Patent No. 10-0604975, PCT/KR2004/003088, PCT/KR2007/001001, and Korean Patent Application No. 2006-0018921, and zinc-containing metal oxide nanoparticles were prepared according to Example 1. As a result, as shown in FIG. 4, Ni and Co-containing nanoparticles showed decreased saturation magnetization when compared to iron oxide nanoparticle matrix (114 emu/g (magnetic atom)). In the case of manganese-containing nanoparticles, the saturation magnetization is 125 emu/g (magnetic atom) which is slightly increased than that of iron oxide. However, in the case of zinc-containing iron oxide nanoparticles, the saturation magnetization is $Zn_{0.4}Fe_{2.6}O_4$ 161 emu/g (magnetic atom) and $Zn_{0.4}Mn_{0.6}Fe_2O_4$ 175 emu/g (magnetic atom), which are increased by 47 and 61 emu/g (magnetic atom), respectively, when compared to the matrix, iron oxide.

It has been known that the T2 MRI contrast effect is directly correlated with the square of the saturation magnetization (Koenig, S. H. et al. *Magn. Reson. Med.* 1995, 34, 227-233). Therefore, it can be expected that the zinc-containing nanoparticles of the present invention will have significantly improved MRI contrast effect.

Example 6

Comparison of the MRI Effects of the Metal Ferrite Nanoparticles Free of Zinc ($MFe_2O_4$, M=Mn, Fe, Co, or Ni) and the Zinc-Containing Metal Ferrite Nanoparticles ($Zn_{0.3}M_{0.7}Fe_2O_4$, M=Mn, Fe, Co, or Ni)

It was confirmed that the zinc-containing metal oxide nanoparticles had superior MRI contrast effect when zinc is contained in various types of nanoparticle matrix as the nanoparticle matrix is changed. To achieve this, various types of zinc-containing metal oxide nanoparticles ($Zn_{0.3}M_{0.7}Fe_2O_4$, M=Mn, Fe, Co, or Ni) that were synthesized in Examples 1 to 5 and metal oxide nanoparticles $MFe_2O_4$ (M=Mn, Fe, Co, or Ni) that did not contain zinc were synthesized, and the T2 spin echo MRI contrast effects of the metal oxide nanoparticles were compared to each other. The obtained nanoparticles had the spherical shape and the uniform size of 15 nm as shown in FIGS. 5A and 5B, and the surfaces of the nanoparticles were coated with dimercaptosuccinic acid.

In order to demonstrate the contrast effects of the magnetic resonance imaging of the obtained nanoparticles, the fast spin echo (FSE) T2 MRI was measured. For the measurement, the 3 T system (Achieva; Philips Medical Systems, Best, The Netherlands) equipped with the sense-flex-M coils was used. The magnetic resonance imaging results were obtained by using the T2-FSE sequence. Specific parameters were as follows: resolution 256 μm×256 μm, slice thickness 1 mm, TE=100 ms, TR=4000 ms, FOV=10×10 cm², and 2 excitations.

Figure 5:
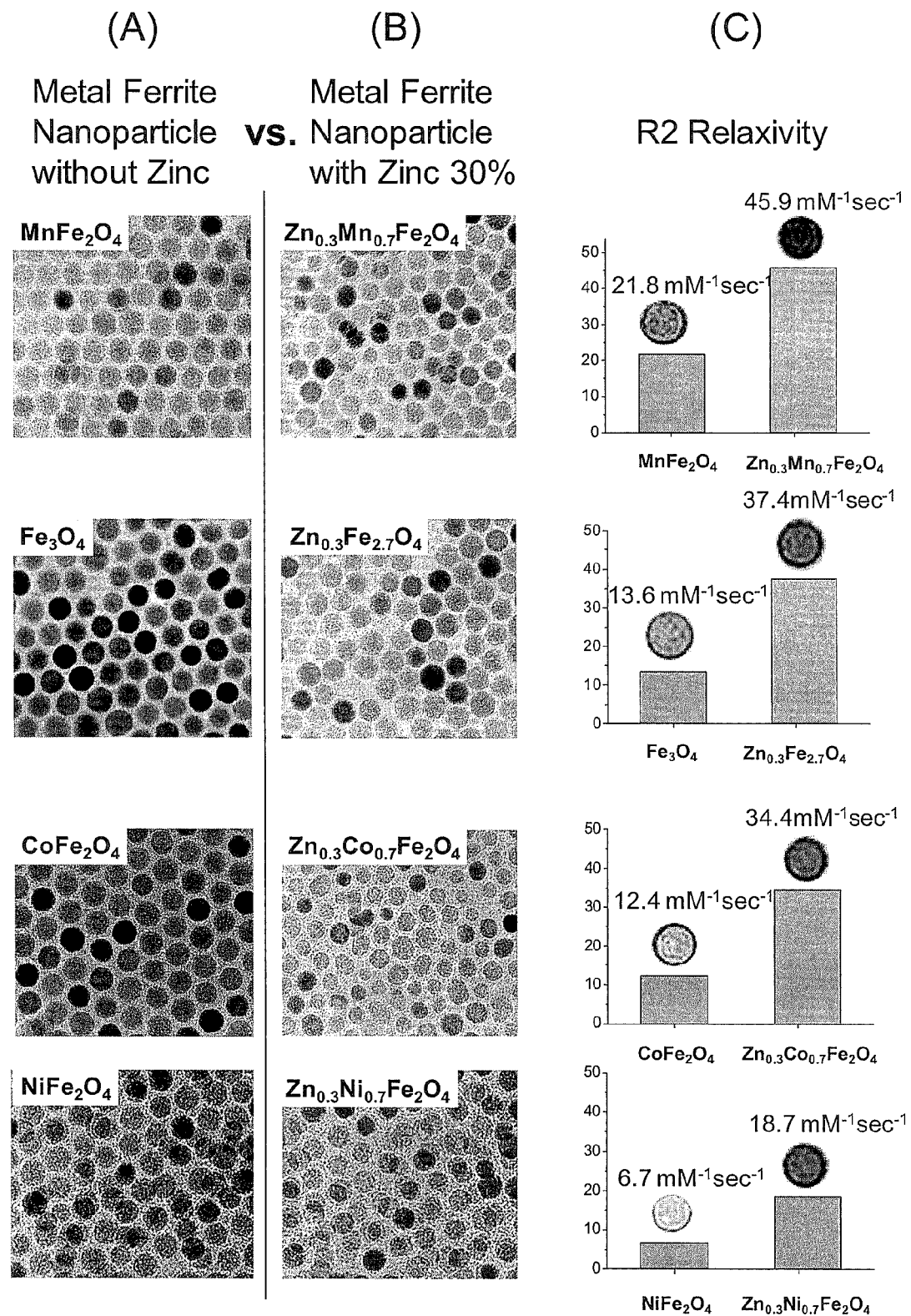
FIG. 5 illustrates comparison in the MRI contrast effect of various zinc-free metal ferrites ($MFe_2O_4$, M=Mn, Fe, Co, and Ni) with zinc-containing metal ferrite ($Z_{0.3}M_{0.7}Fe_2O_4$).
Figure 6:
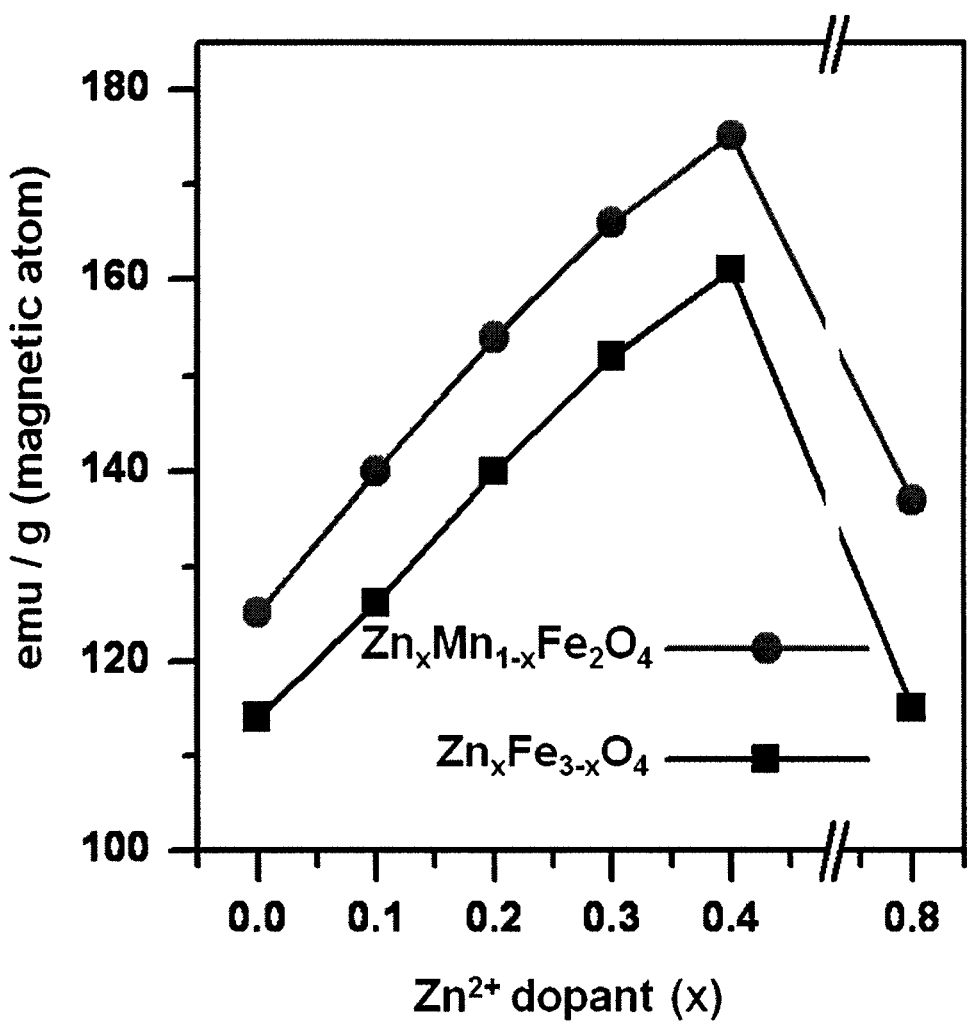
FIG. 6 illustrates saturation magnetization of an MRI contrast agent comprising zinc-containing magnetic metal ferrite nanoparticles, according to zinc content.

As shown in FIG. 5C, it was found that the zinc-containing metal ferrite ($Zn_{0.3}M_{0.7}Fe_2O_4$) exhibited approximately 2~3 fold increase in MRI signal (dark color) as compared to the metal ferrite ($MFe_2O_4$) that did not contain zinc. In the case of the R2 relaxivity coefficient (R2 changing ratio according to concentration), a measurement of a contrast effect, it was found that the zinc-containing manganese ferrite $Zn_{0.3}Mn_{0.7}Fe_2O_4$ had the relaxivity coefficient of 45.9 $mM^{-1}$ $sec^{-1}$, which was an even more increased value as compared to that of the manganese ferrite that did not contain zinc, 21.8 $mM^{-1}$ $sec^{-1}$. In respects to $Zn_{0.3}Fe_{0.7}Fe_2O_4$, $Zn_{0.3}CO_{0.7}Fe_2O_4$, and $Zn_{0.3}Ni_{0.7}Fe_2O_4$, the relaxivity coefficient was 37.4 $mM^{-1}$ $sec^{-1}$, 34.4 $mM^{-1}$ $sec^{-1}$, and 18.7 $mM^{-1}$ $sec^{-1}$, which was increased as compared to 13.6 $mM^{-1}$ $sec^{-1}$, 12.4 $mM^{-1}$ $sec^{-1}$, and 6.7 $mM^{-1}$ $sec^{-1}$ of $Fe_3O_4$, $CoFe_2O_4$, and $NiFe_2O_4$ that did not contain zinc.

Example 7

Comparison of Saturation Magnetization of $Zn_xM_{1-x}Fe_2O_4$ (M=Fe or Mn, x=0, 0.1, 0.2, 0.3, 0.4, and 0.8) According to Zinc Content The effect of zinc content onto saturation magnetization and MRI contrast effect was confirmed. To achieve this, $Zn_xM_{1-x}Fe_2O_4$ (M=Fe or Mn, x=0, 0.1, 0.2, 0.3, 0.4, and 0.8) having 15 nm size were synthesized according to Example 1. The saturation magnetization at 3 Tesla was measured using an MPMS SQUID Magnetometer.

The saturation magnetization ($M_s$) of each the $Zn_xMn_{1-x}Fe_2O_4$ (x=0, 0.1, 0.2, 0.3, 0.4, and 0.8) nanoparticle was 125, 140, 154, 166, 175, and 137 emu/g (magnetic atom) respectively and similarly the saturation magnetization ($M_s$) of each the $Zn_xFe_{3-x}O_4$ (x=0, 0.1, 0.2, 0.3, 0.4, and 0.8) was 114, 126, 140, 152, 161, and 115 emu/g $Zn_{0.4}Fe_{2.6}O_4$ (magnetic atom).

Both nanoparticles showed maximum $M_s$ at x=0.4 of $Zn_{0.4}Fe_{2.6}O_4$ 161 emu/g (magnetic atom), $Zn_{0.4}Mn_{0.6}Fe_2O_4$ 175 emu/g (magnetic atom), which are the highest than any metal oxide discovered until now.

Example 8

Comparison of R2MR Relaxivity of $Zn_xM_{1-x}Fe_2O_4$ (M=Fe or Mn, x=0, 0.1, 0.2, 0.3, 0.4, 0.8) According to Zinc Content Whether the change of the saturation magnetization of $Zn_xM_{1-x}Fe_2O_4$ which was confirmed in Example 7 increases MRI contrast effect was confirmed. To achieve this, MRI contrast effect of $Zn_xM_{1-x}Fe_2O_4$ (M=Fe or Mn, x=0, 0.1, 0.2, 0.3, 0.4, 0.8) nanoparticles was measured, using 3 T MRI system (Achieva; Philips Medical Systems, Best, The Netherlands) equipped with the sense-flex-M coils was used. The magnetic resonance imaging results were obtained by using FSE sequence. Specific parameters were as follows: resolution 256 μm×256 μm, slice thickness 1 mm, TE=100 ms, TR=400 ms, FOV=10×10 cm², and 2 excitations.

Figure 7:
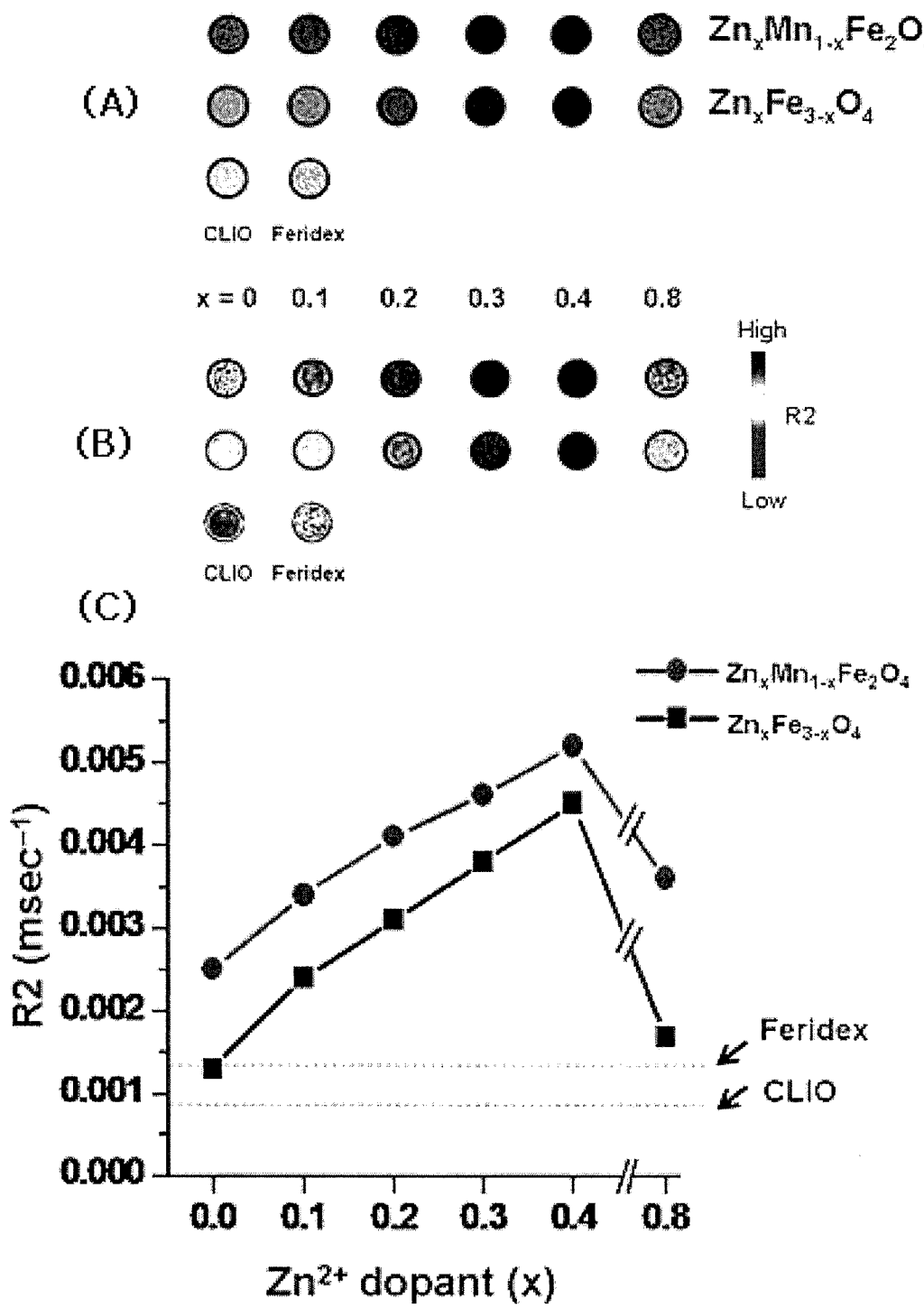
FIG. 7 illustrates MRI signals of MRI contrast agents comprising zinc-containing magnetic metal ferrite nanoparticles, according to zinc content. (7A) T2 fast spin echo MRI of $Zn_xMn_{1-x}Fe_2O_4$, x=0, 0.1, 0.2, 0.3, 0.4, and 0.8 and $Zn_xFe_{3-x}O_4$, x=0, 0.1, 0.2, 0.3, 0.4, and 0.8 nanoparticles and Feridex, CLIO (cross linked iron oxide), (7B) a color coded image of image 7A, (7C) R2 relaxivity graph according to zinc content.

As shown in FIG. 7A, both nanoparticles of $Zn_xMn_{1-x}Fe_2O_4$ and $Zn_xFe_{3-x}O_4$ show that T2 MRI signal changed to dark color (changed to blue in colored image FIG. 7B) as zinc content increased. It was confirmed that $Zn_xMn_{1-x}Fe_2O_4$ (x=0, 0.1, 0.2, 0.3, 0.4, 0.8) nanoparticles have R2 of 0.0025, 0.0034, 0.0041, 0.0046, 0.0052, 0.0036 $msec^{-1}$, respectively at the same concentration (based on a metal atom). In the same manner, $Zn_xM_{3-x}O_4$ (x=0, 0.1, 0.2, 0.3, 0.4, and 0.8) nanoparticles have R2 of 0.0012, 0.0024, 0.0031, 0.0038, 0.0045, 0.0016 $msec^{-1}$, respectively (FIG. 7C). In particular, when x=0.4 R2 is 0.0052 and 0.0045 $msec^{-1}$, respectively at the two nanoparticles; when compared to those of Feridex (0.0015 $msec^{-1}$) and CLIO (0.0008 $msec^{-1}$) that was the conventional iron oxide nanoparticle contrast agent, the $Zn_{0.4}Mn_{0.6}Fe_2O_4$ nanoparticles the superior contrast effect of about 350% and 650% as high as that of Feridex and CLIO, respectively, and in the case of the $Zn_{0.4}Fe_{2.6}O_4$, the contrast effect was about 300% and 560% as high as that of Feridex and CLIO, respectively.

Example 9

Synthesis of Zinc-Containing Ferrite Nanoparticles in an Aqueous Solution, $Zn_xFe_{3-x}O_4$ (x=0.2, 0.4) Composition An MRI contrast agent comprising zinc-containing metal oxide nanoparticles of the present invention is not prepared exclusively by the phase transition process described in the above, but can be prepared by the following method:

In order to synthesize zinc-containing iron oxide nanoparticles having the formula of $Zn_xFe_{3-x}O_4$ (x=0.2 and 0.4) in an aqueous solution, a precursor of nanoparticle, $Zn(acac)_2 \cdot 2H_2O$ 20 mg, $FeCl_2 \cdot 4H_2O$ 60 mg, and $FeCl_3 \cdot 6H_2O$ 240 mg were dissolved in 10 ml water, and then 1 ml of 3.2 M $NH_4OH$ solution was added, vigorously stirred for 20 minutes to obtain $Zn_{0.2}Fe_{2.8}O_4$ nanoparticles. In order to obtain $Zn_{0.4}Fe_{2.6}O_4$ nanoparticles, 40 mg of each of the precursors $Zn(acac)_2 \cdot 2H_2O$, $FeCl_2 \cdot 4H_2O$ were used under the same condition.

Figure 8:
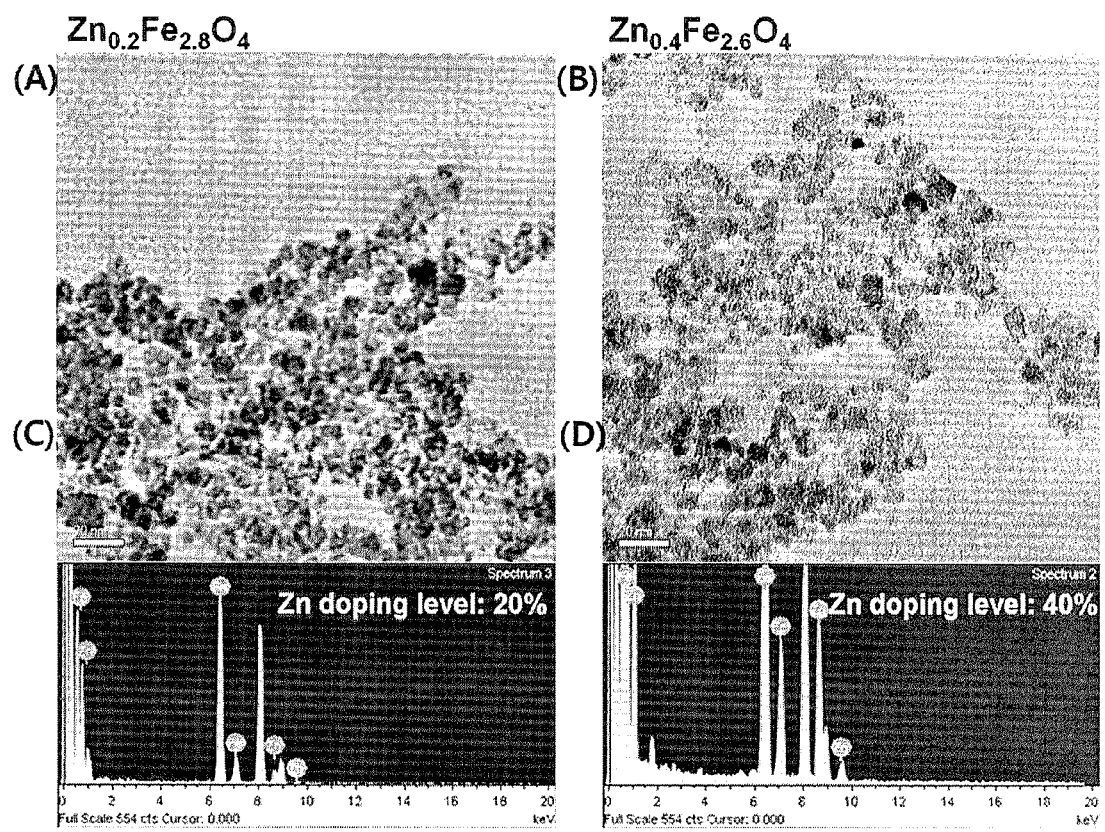
FIG. 8 illustrates zinc-containing iron oxide nanoparticles which were synthesized in an aqueous solution ($Zn_xFe_{3-x}O_4$, x=0.2, 0.4). (8A, 8B) TEM images, and (8C, 8D) EDAX analyses.
Figure 9:
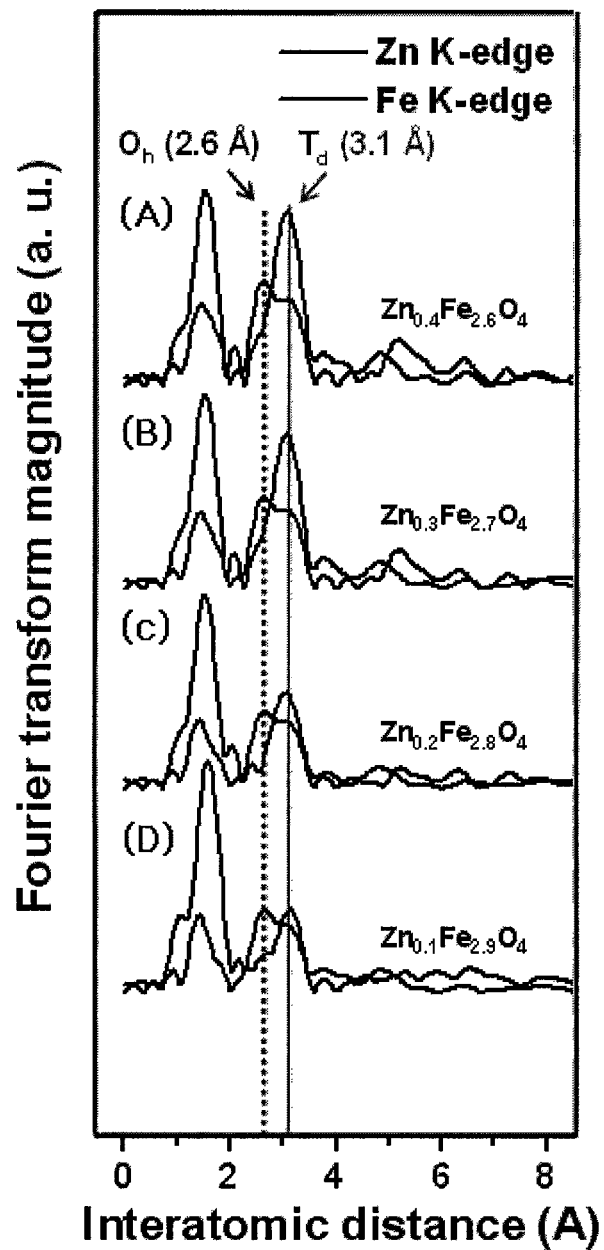
FIG. 9. Extended X-ray absorption fine structure (EXAFS) spectra according to zinc content in zinc-containing ferrite nanoparticles. $Zn_xFe_{3-x}O_4$ (x=(9A) 0.4, (9B) 0.3, (9C) 0.2, (9D) 0.1).

FIG. 8 shows the electron microscope picture of $Zn_xFe_{3-x}O_4$ (x=0.2, and 0.4) nanoparticles synthesized according to the above method (FIGS. 8A and 8B) and the analysis of zinc content through EDAX (FIGS. 8C and 8D). It was confirmed that zinc containing nanoparticles can be prepared according to the above method and the zinc content can be controlled. The synthesized nanoparticles did not have fixed shapes and had about 15 nm size.

Example 10

EXAFS Analysis of Zinc-Containing Ferrite Nanoparticles

In order to see the distribution of zinc in the ferrite matrix of zinc-containing ferrite nanoparticles of the present invention, EXAFS was measured. FIGS. 9A to 9D show Zn K-edge and Fe K-edge EXAFS spectrum of $Zn_xFe_{3-x}O_4$ (x=0.1, 0.2, 0.3, 0.4) nanoparticles which was prepared according to Example 1. In the Zn K-edge spectrum, the peaks in 3.1 angstrom and 2.6 angstrom show zinc present in a tetrahedron hole ($T_d$) and an octahedron hole ($O_h$) in the matrix, respectively. The fact that 3.1 angstrom peak is strong and that it is selectively increasing when zinc content ratio (x) increases shows that zinc is selectively distributed on tetrahedron interstitial holes. Such result is a phenomenon which is outstanding when nanoparticles are prepared in an organic solvent, indicating that this preparation method is more effectively incorporating zinc that the preparation method in aqueous solution.

Example 11

Synthesis of a Zinc-Containing Metal Oxide Nanoparticle MRI Contrast Agent Coated with BSA (Bovine Serum Albumin)

The zinc-containing metal oxide nanoparticles that were synthesized in Examples 1 to 4 and dispersed in 1 ml of toluene in a concentration of 50 mg/ml were precipitated with an excessive amount of ethanol, and redispersed in 5 ml solution of 1M TMAOH solution. Next, 200 mg of BSA was added and dissolved, and reacted at room temperature for 24 hours. Subsequently, the reaction solution was separated with a Sephacryl S-500 column (GE Healthcare, USA) to remove excess BSA which did not react with the nanoparticles and to separate the nanoparticles. The separated nanoparticles were concentrated to 5 ml by using a Centricon YM100 filter (Millipore, USA).

Example 12

Synthesis of a Zinc-Containing Metal Oxide Nanoparticle MRI Contrast Agent Coated with Carbodextran 200 mg of carbodextran was added to 5 ml of TMAOH-coated nanoparticles, which were synthesized by the same method as that of Example 11, and then dispersed therein, and the reaction was performed at room temperature for 24 hours. Subsequently, the reaction solution was separated with a Sephacryl S-500 column to remove the excess carbodextran which did not react with the nanoparticles and to separate the nanoparticles. The separated nanoparticles were concentrated to 5 ml with a Centricon YM100 filter.

Example 13

Synthesis of a Zinc-Containing Metal Oxide Nanoparticle MRI Contrast Agent Coated with Hypromelose 100 mg of hypromelose was added to 5 ml of TMAOH-coated nanoparticles that were synthesized by the same method as that of Example 11 and then dissolved therein, and the reaction was performed at room temperature for 24 hours. Subsequently, the reaction solution was separated by using a Sephacryl S-500 column to remove the excess hypromelose which did not react with the nanoparticles and to separate the nanoparticles. The separated nanoparticles were concentrated to 5 ml with a Centricon YM100 filter.

Example 14

Synthesis of a Zinc-Containing Metal Oxide Nanoparticle MRI Contrast Agent Coated with Neutravidin 100 mg of neutravidin was added to 5 ml of nanoparticles that were synthesized by the same method as that of Example 11 and then dissolved therein, and the reaction was performed at room temperature for 24 hours. Subsequently, the reaction solution was separated with a Sephacryl S-500 column to remove the excess neutravidin which did not react with the nanoparticles and to separate the nanoparticles. The separated nanoparticles were concentrated to 5 ml with a Centricon YM100 filter.

Example 15

Synthesis of a Zinc-Containing Metal Oxide Nanoparticle MRI Contrast Agent Coated with the Antibody (IgG)

100 mg of antibody was added to 5 ml of nanoparticles that were solubilized in water and synthesized by the same method as that of Example 11 and then dissolved therein, and the reaction was performed at room temperature for 24 hours. Subsequently, the reaction solution was separated with a Sephacryl S-500 column to remove the excess antibody which did not react with the nanoparticles and to separate the nanoparticles. The separated nanoparticles were concentrated to 5 ml with a Centricon YM100 filter.

Example 16

Figure 10:
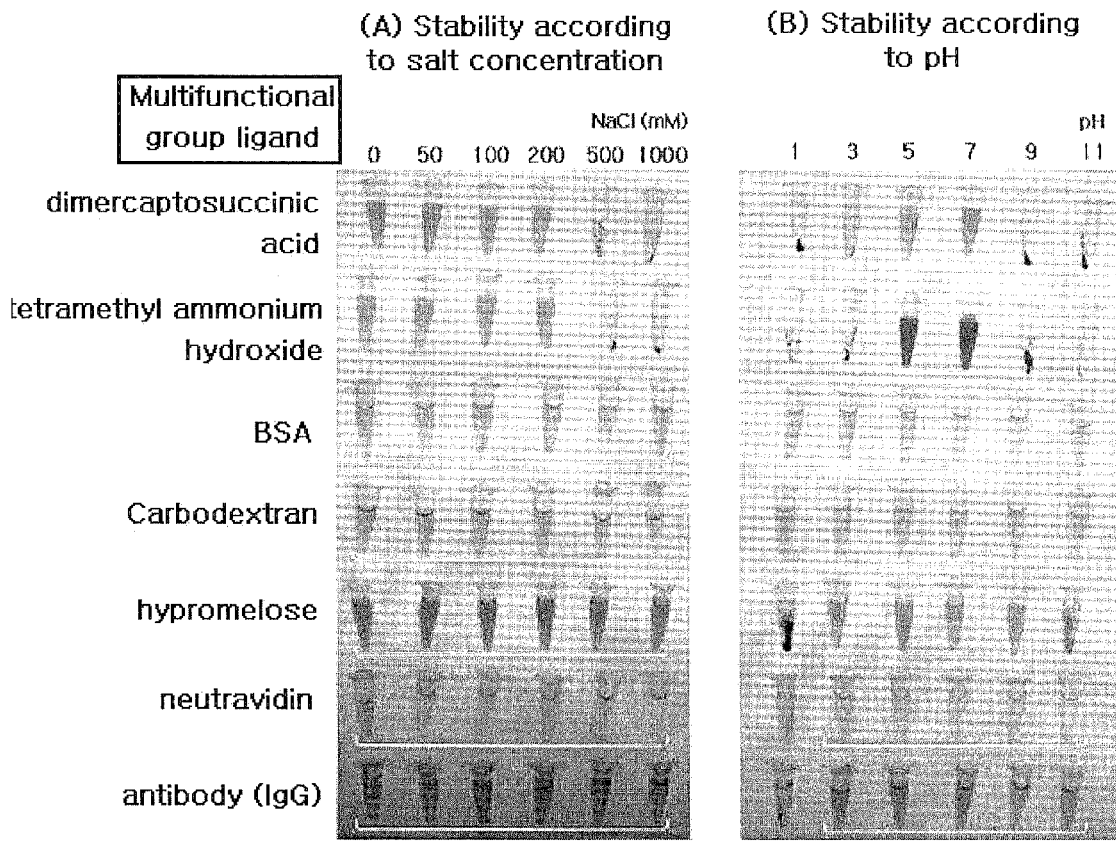
FIG. 10 illustrates the stability test in respects to the various aqueous solutions of the zinc-containing MRI contrast agent ($Zn_{0.4}Fe_{2.6}O_4$) that is subjected to the surface modification by using the water soluble multi-functional group ligand and dispersed in water.

Analysis on the Stability According to pH and Salt Concentration of the MRI Contrast Agent Comprising the Zinc-Containing Metal Oxide Nanoparticles The stability according to pH and salt concentration of the MRI contrast agent that comprises the zinc-containing metal oxide nanoparticles which were coated with a variety of ligand was analyzed. As shown in FIG. 10A, the water soluble nanoparticles were stable with respects to the concentration of 200 mM NaCl, and in particular, BSA-$Zn_{0.4}Fe_{2.6}O_4$, carbodextran-$Zn_{0.4}Fe_{2.6}O_4$, hypromelose-$Zn_{0.4}Fe_{2.6}O_4$, neutravidin-$Zn_{0.4}Fe_{2.6}O_4$, and antibody (IgG)-$Zn_{0.4}Fe_{2.6}O_4$ nanoparticles were stable in respects to the concentration of 1 M or more.

In addition, as shown in FIG. 10B, all the water soluble nanoparticles were stable in the range of pH 7 to 9, and in particular, the BSA-$Zn_{0.4}Fe_{2.6}O_4$ and carbodextran-$Zn_{0.4}Fe_{2.6}O_4$ nanoparticles were stable in the range of pH 1 to 11.

Example 17

Contrasting of a Liver of a Mouse Using the MRI Contrast Agent Comprising the Zinc-Containing Metal Oxide Having $Zn_{0.4}Fe_{2.6}O_4$ In order to confirm the MRI contrast effect of the MRI contrast agent comprising the zinc-containing metal oxide in vivo, the $Zn_{0.4}Fe_{2.6}O_4$ nanoparticles coated with BSA which were synthesized in Example 11 were intravenously injected through the tail of the Balb/c mouse (n=4) in a concentration of 2 mg/ml and a dose of 8 mg/kg. MRI was measured every 10 minutes before and after the injection of the nanoparticles. In connection with this, the T2 signal intensity was measured in order to confirm the contrast effect of the liver of the nanoparticles.

In order to measure the MRI, the 3 T system (Achieva; Philips Medical Systems, Best, The Netherlands) equipped with the sense-flex-M coils was used. The magnetic resonance imaging results were obtained by using FSE sequence.

Specific parameters were as follows: resolution 256 µm×256 µm, slice thickness 1 mm, TE=100 ms, TR=4000 ms, FOV=10×10 $cm^2$, and 2 excitations.

Figure 11:
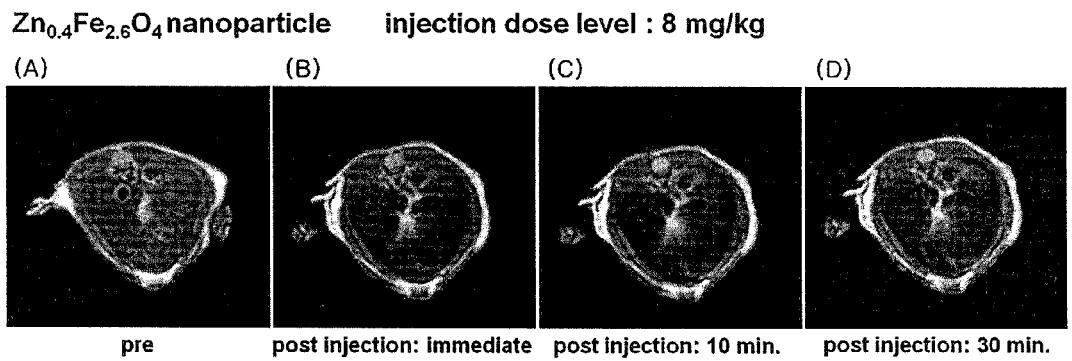
FIG. 11 illustrates the MR image of a mouse liver in which MRI contrast agent comprising zinc-containing ferrite magnetic nanoparticles ($Zn_{0.4}Fe_{2.6}O_4$, core size: 15 nm) is injected via tail vein.

As shown in FIG. 11, it was found that after the nanoparticles were injected, the T2 magnetic resonance image signal of the liver was reduced to make the liver dark. In general, the dose of 25 mg/kg of iron oxide contrast agent is used for the test of the mouse. Comparatively, in the case of the MRI contrast agent comprising the zinc-containing metal oxide disclosed in the present patent, the effective contrast image of the liver was obtained even though the dose of 8 mg/kg, which was about ⅓ of the conventional dose level.

Example 18

Figure 12:
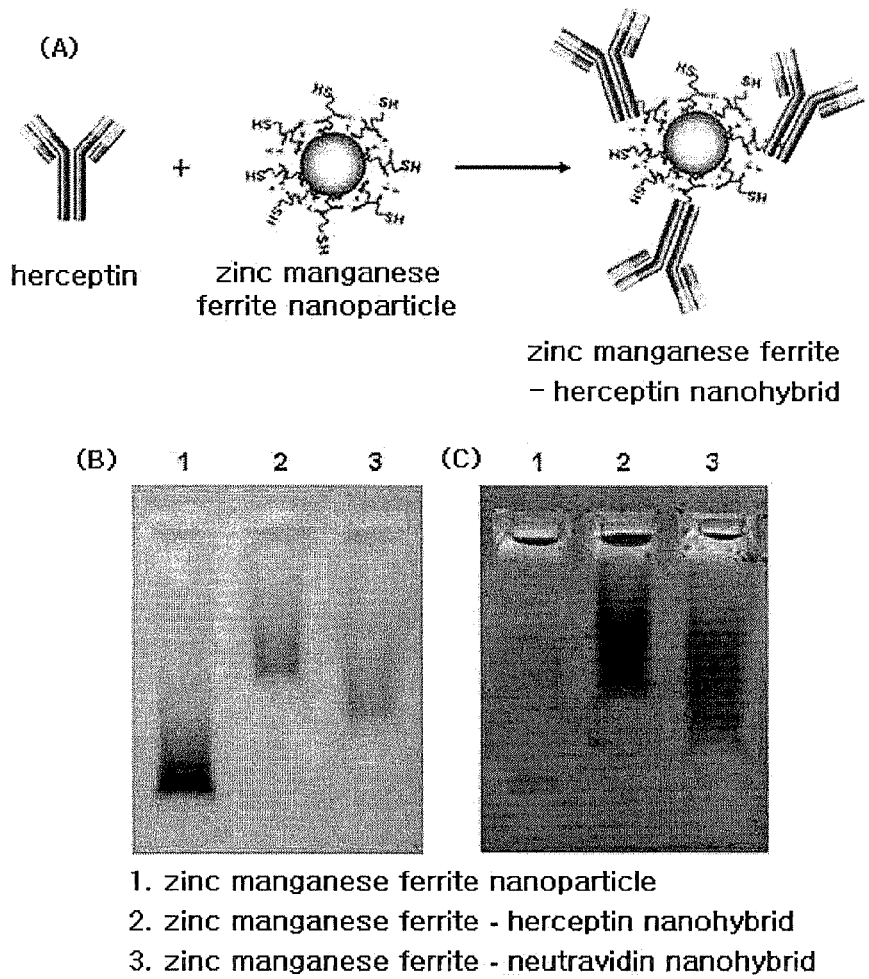
FIG. 12 illustrates the production of hybrid nanoparticles of zinc-containing metal oxide nanoparticle and bio-material (12A) in which the biomaterial is conjugated with the zinc manganese ferrite nanoparticles, and (12B) the electrophoresis and (12C) protein staining.

Synthesis of 'Zinc-Containing Metal Oxide Nanoparticles ($Zn_{0.4}Mn_{0.6}Fe_2O_4$)—Biologically/Chemically Active Material (Herceptin)' Hybrid Nanoparticles The schematic production procedure of nano hybrid is shown in FIG. 12. After 100 µl of herceptin [(10 mg/ml in the 10 mM phosphoric acid buffer solution, pH 7.2) Genentech, Inc., South San Francisco, Calif., USA] was put in an eppendorf tube, sulfo-SMCC [(N-Maleimidomethyl)cyclohexane-1-carboxylic acid 3-sulfo-N-hydroxy-succimide ester, Pierce] was added thereto and the reaction was performed at room temperature for 30 min to substitute the lysine group of herceptin with the maleimide group. Herceptin in which the lysine group was substituted with the maleimide group was reacted with the solution that included 200 µl of dimercaptosuccinic acid-coated $Zn_{0.4}Mn_{0.6}Fe_2O_4$ at room temperature for 4 hours to prepare the zinc-containing manganese ferrite-herceptin nanohybrid particles. The prepared nano hybrid particles were analyzed by agarose electrophoresis. From the Coomassie Blue protein dyeing results, it could be seen that the nano hybrid was generated (FIG. 12C, Lane 2).

Example 19

Synthesis of 'Zinc-Containing Metal Oxide Nanoparticles ($Zn_{0.4}Mn_{0.6}Fe_2O_4$)—Biologically/Chemically Active Material (Neutravidin)' Hybrid Nanoparticles After 100 μl of neutravidin [(10 mg/ml in the 10 mM phosphoric acid buffer solution, pH 7.2), Sigma] was put in an eppendorf tube, sulfo-SMCC was added thereto and the reaction was performed at room temperature for 30 min to substitute the lysine group of neutravidin with the maleimide group. Neutravidin substituted with the maleimide group was reacted with the solution that included 200 μl of dimercaptosuccinic acid-coated $Zn_{0.4}Mn_{0.6}Fe_2O_4$ at room temperature for 4 hours to prepare the zinc manganese ferrite-neutravidin nanohybrid particles. The prepared nano hybrid particles were analyzed by agarose electrophoresis. From the Coomassie Blue protein dyeing results, it could be seen that the nano hybrid was generated (FIG. 12C, Lane 3).

Example 20

Figure 13:
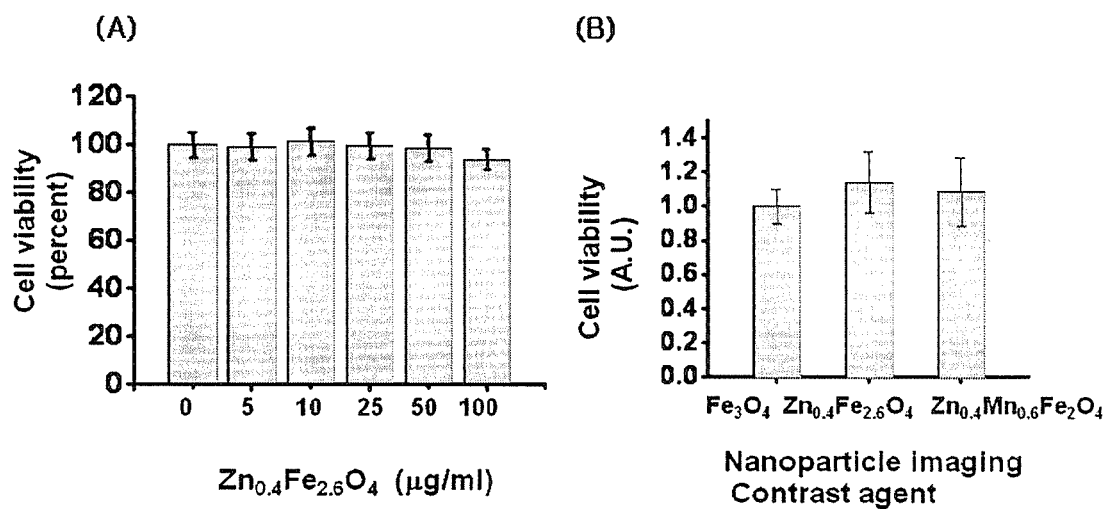
FIG. 13 illustrates the cytotoxicity of the MRI contrast agent that includes the zinc-containing metal oxide nanoparticles. (13A) Comparison of cell viability according to the treatment amount of the zinc-containing magnetic nanoparticle contrast agent ($Zn_{0.4}Fe_{2.6}O_4$) (13B) Comparison of cell viability of the iron oxide ($Fe_3O_4$) and zinc-containing magnetic nanoparticle contrast agent ($Zn_{0.4}Fe_{2.6}O_4$ and $Zn_{0.4}Mn_{0.6}Fe_2O_4$) at the treatment amount of 100 µg/ml.

Comparison of Cytotoxicity of the MRI Contrast Agents Comprising the Zinc-Containing Metal Oxide Nanoparticles The cytotoxicity of the MRI contrast agent comprising the zinc-containing metal oxide nanoparticles was evaluated. $2 \times 10^5$ HeLa cells were treated with dimercaptosuccinic acid-treated $Zn_{0.4}Fe_{2.6}O_4$ having the size of 15 nm with varying concentration. After 24 hours, the cell viability was measured by a trypan blue method. As shown in FIG. 13A, the cell viability was maintained to almost 100% viability up to a concentration of 100 μg/ml of $Zn_{0.4}Fe_{2.6}O_4$, indicating that the nanoparticles are biocompatible. In addition, as shown in FIG. 13B, at a concentration of 100 μg/ml ferrite and manganese ferrite nanoparticles showed similar cell viabilities. When considering the fact that ferrite nanoparticles are approved for a human use by the U.S. FDA, the zinc-containing nanoparticles have advantages for being bio-compatible.

Example 21

Nano Hybrid System for Optic-MRI Double Mode Diagnosis

Figure 14:
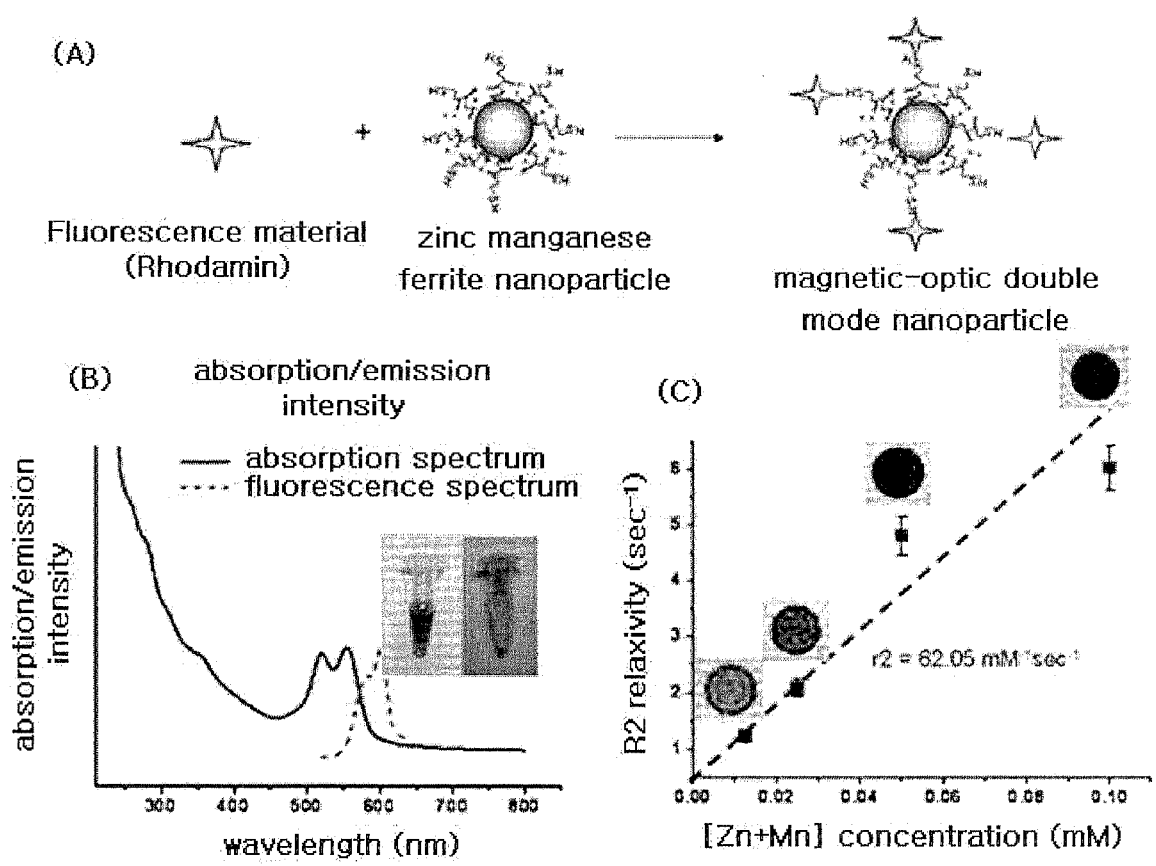
FIG. 14 illustrates the magnetic-optic dual mode nanoparticles that are obtained by conjugating the zinc manganese ferrite nanoparticles to the fluorescent dye (Rhodamin).

In order to develop a diagnosis probe having both the optical property and the magnetic property, a fluorescent dye (rhodamine isothocyanate, RITC) was attached to the zinc-containing manganese ferrite nanoparticles that were subjected to surface stabilization by using BSA (FIG. 14A). To achieve this, an excessive amount of NHS-FITC having the molar ratio that was about 20 times as high as that of —$NH_2$ present in bovine serum albumin was added thereto. Then it was reacted in the 10 mM phosphate buffered saline at normal temperature for 2 hours to synthesize the rhodamine-zinc manganese ferrite hybrid nanoparticles. In result, as shown in FIG. 14, the optic-magnetic hybrid particles had the fluorescent property (FIG. 14B) and the magnetic resonance image signal (FIG. 14C).

The invention claimed is:

1. An MRI contrast agent comprising zinc-containing metal oxide nanoparticles have a chemical formula of:
   (a) $Zn_xFe_{3-x}O_4$, wherein x=0.1-0.4,
   wherein the dispersibility of the zinc-containing metal oxide nanoparticles to water is in the range of 1 μg/ml to 500 mg/ml, and the hydrodynamic diameter of the nanoparticles that are dispersed in water is in the range of 1 nm to 500 μm; wherein the zinc-containing metal oxide nanoparticle itself is dispersed in water, or the zinc-containing metal oxide nanoparticle is coated with water-soluble multi-functional group ligands to be dispersed in an aqueous solution; wherein the zinc-containing metal oxide nanoparticles have a saturation magnetization of 100 emu/g or more (magnetic atom), wherein the zinc-containing metal oxide nanoparticles are prepared by a method comprising synthesizing water-insoluble, zinc-containing nanoparticles in organic solvents, and wherein the zinc-containing metal oxide nanoparticles comprise zinc incorporated into a tetrahedron interstitial hole.

2. The MRI contrast agent as set forth in claim 1, wherein x=0.2-0.4.

3. The MRI contrast agent as set forth in claim 1, wherein x=0.4.

4. An MRI contrast agent comprising zinc-containing metal oxide nanoparticles have a chemical formula of:
   $Mn_{1-x}Zn_xFe_2O_4$; wherein x=0.1-0.4,
   wherein the dispersibility of the zinc-containing metal oxide nanoparticles to water is in the range of 1 μg/ml to 500 mg/ml, and the hydrodynamic diameter of the nanoparticles that are dispersed in water is in the range of 1 nm to 500 μm; wherein the zinc-containing metal oxide nanoparticle itself is dispersed in water, or the zinc-containing metal oxide nanoparticle is coated with water-soluble multi-functional group ligands to be dispersed in an aqueous solution; wherein the zinc-containing metal oxide nanoparticles have a saturation magnetization of 100 emu/g or more (magnetic atom), wherein the zinc-containing metal oxide nanoparticles are prepared by a method comprising synthesizing water-insoluble, zinc-containing nanoparticles in organic solvents, and wherein the zinc-containing metal oxide nanoparticles comprise zinc incorporated into a tetrahedron interstitial hole.

5. The MRI contrast agent as set forth in claim 4, wherein x=0.2-0.4.

* * * * *